(12) United States Patent
Choi et al.

(10) Patent No.: US 12,703,730 B2
(45) Date of Patent: Aug. 11, 2026

(54) LONG-ACTING CONJUGATES OF GLP-2 DERIVATIVES

(71) Applicant: HANMI PHARM. CO., LTD., Hwaseong-si (KR)

(72) Inventors: Jaehyuk Choi, Hwaseong-si (KR); Min Young Kim, Hwaseong-si (KR); In Young Choi, Hwaseong-si (KR); Sung Youb Jung, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 17/721,048

(22) Filed: Apr. 14, 2022

(65) Prior Publication Data

US 2022/0251164 A1 Aug. 11, 2022

Related U.S. Application Data

(60) Division of application No. 16/832,634, filed on Mar. 27, 2020, now Pat. No. 11,530,249, which is a continuation of application No. PCT/KR2018/011586, filed on Sep. 28, 2018.

(30) Foreign Application Priority Data

Sep. 28, 2017 (KR) ........................ 10-2017-0126577

(51) Int. Cl.
*C07K 14/605* (2006.01)
*A61K 47/62* (2017.01)
*A61K 47/68* (2017.01)
*A61P 1/00* (2006.01)

(52) U.S. Cl.
CPC ............ *C07K 14/605* (2013.01); *A61K 47/62* (2017.08); *A61K 47/68* (2017.08); *A61P 1/00* (2018.01)

(58) Field of Classification Search
CPC .. C07K 14/605; C07K 2317/52; C07K 16/00; C07K 2319/00; C07K 14/575; C07K 2317/55; C07K 2317/94; C07K 14/765; A61P 3/10; A61P 3/00; A61P 3/08; A61P 5/50; A61K 38/00; A61K 38/26; A61K 47/64; A61K 2039/505; A61K 39/00; A61K 49/0056; A61K 47/6889
See application file for complete search history.

(56) References Cited

U.S. PATENT DOCUMENTS

2009/0312259 A1* 12/2009 Bridon ...................... A61P 1/00 530/324
2010/0105877 A1* 4/2010 Song ................ C07K 14/57563 530/391.9
2014/0377290 A1* 12/2014 Kim ...................... A61K 47/60 424/179.1

FOREIGN PATENT DOCUMENTS

| | | | |
|---|---|---|---|
| KR | 10-2008-0064750 | A | 7/2008 |
| KR | 10-2011-0093924 | A | 8/2011 |
| KR | 10-2012-0043205 | A | 5/2012 |
| KR | 10-2013-0078634 | A | 7/2013 |
| KR | 10-2014-0069131 | A | 6/2014 |
| TW | 201333032 | A | 8/2013 |
| TW | I413528 | B | 11/2013 |
| WO | 96/32478 | A1 | 10/1996 |
| WO | 97/34631 | A1 | 9/1997 |
| WO | 2002066511 | | 8/2002 |
| WO | 2005/103087 | A1 | 11/2005 |
| WO | 2006/117565 | A2 | 11/2006 |
| WO | 2006/117565 | A3 | 11/2006 |
| WO | 2010/042145 | A1 | 4/2010 |
| WO | 2013/100704 | A1 | 7/2013 |

OTHER PUBLICATIONS

Esteras et al. Identification of SUMO conjugation sites in the budding yeast proteome. Microbial Cell. 2017; 4(10): 331-341. (Year: 2017).*
Bolette Hartmann et al., "In Vivo and in Vitro Degradation of Glucagon-Like Peptide-2 in Humans*", The Journal of Clinical Endocrinology & Metabolism, 2000, pp. 2884-2888, vol. 85, No. 8.
Eugen Uhlmann et al., "Antisense Oligonucleotides: A New Therapeutic Principle", Chemical Reviews, 1990, pp. 543-584, vol. 90, No. 4.
International Search Report for PCT/KR2018/011586, dated Jan. 3, 2019.
Wisniewski et al., "Synthesis and Pharmacological Characterization of Novel Glucagonlike Peptide-2 (GLP-2) Analogues with Low Systemic Clearance", J. Med. Chem., 2016, vol. 59, pp. 3129-3139 (11 p. total).
Kontermann, "Half-life extended biotherapeutics", Expert Opinion on Biological Therapy, 2016, vol. 16, No. 7, pp. 903-915 (14 pages total).

* cited by examiner

*Primary Examiner* — Melissa L Fisher
*Assistant Examiner* — Jia-Hai Lee
(74) *Attorney, Agent, or Firm* — Sughrue Mion, PLLC

(57) ABSTRACT

A glucagon-like peptide-2 (GLP-2) derivative, a conjugate thereof, and a use thereof are disclosed. Additionally, a method for preparing a glucagon-like peptide-2 (GLP-2) derivative and a conjugate thereof is disclosed.

11 Claims, 4 Drawing Sheets

Specification includes a Sequence Listing.

[Fig. 1]
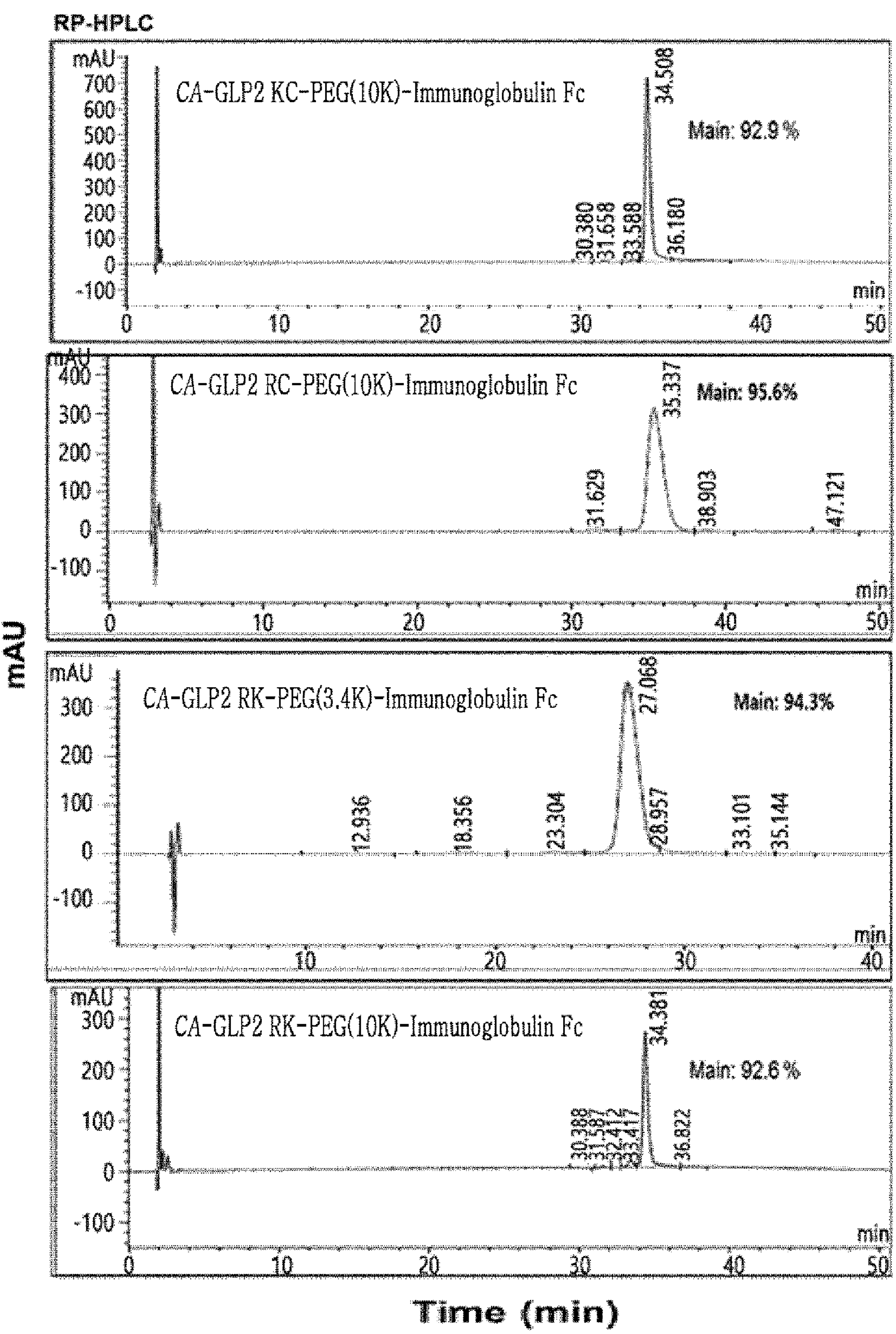

[Fig. 2]
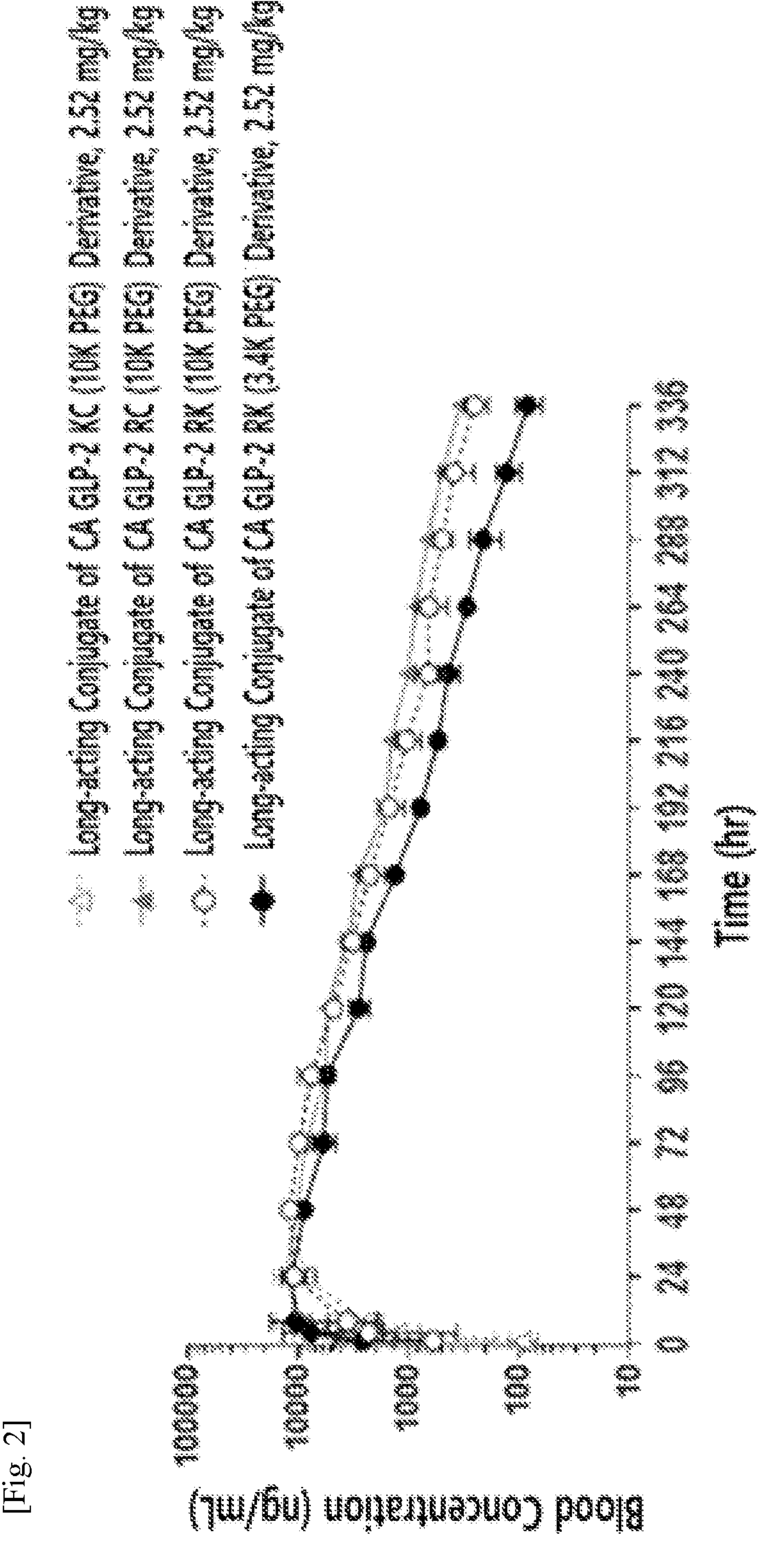

[Fig. 3]
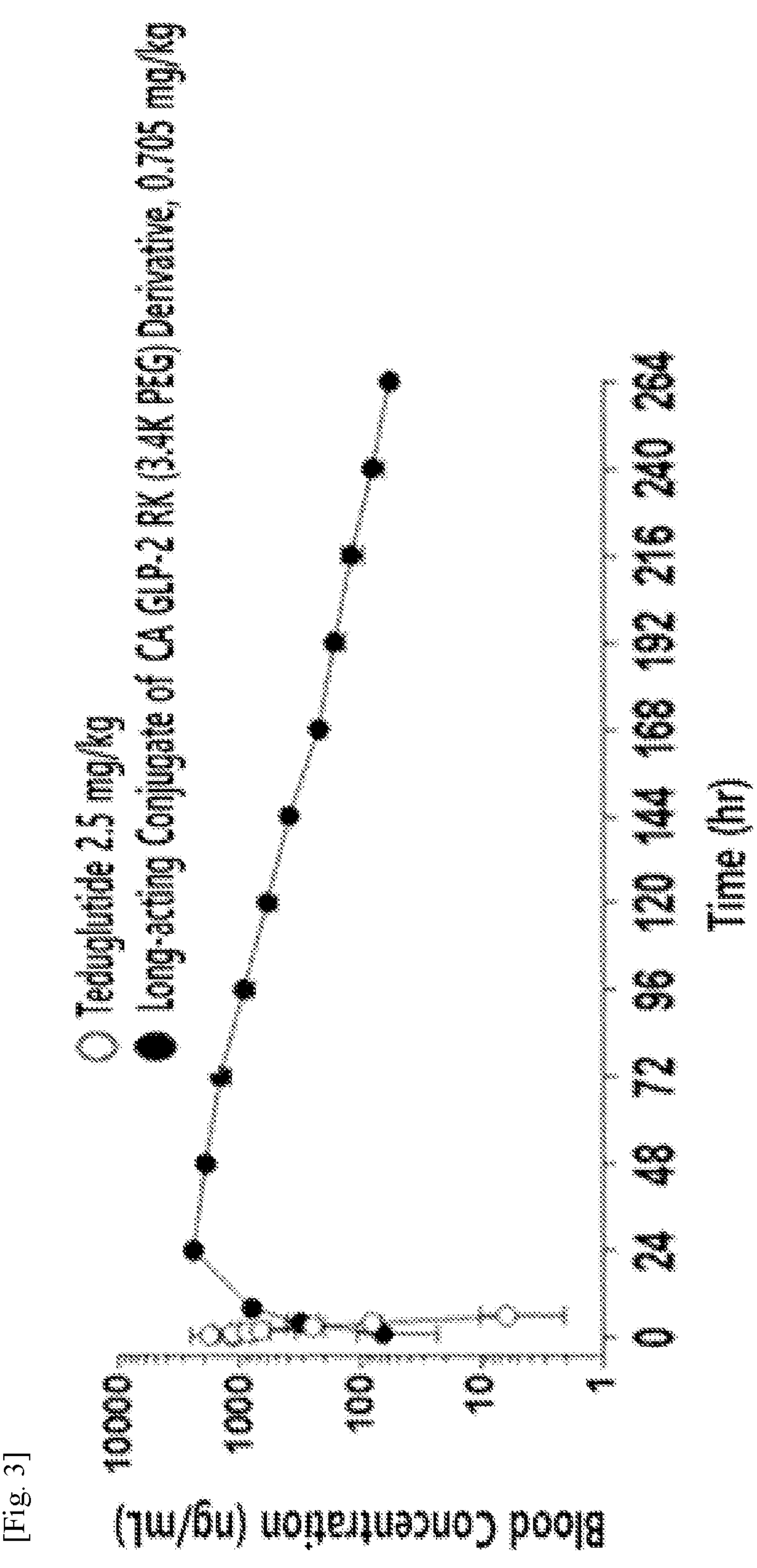

[Fig. 4(A)]
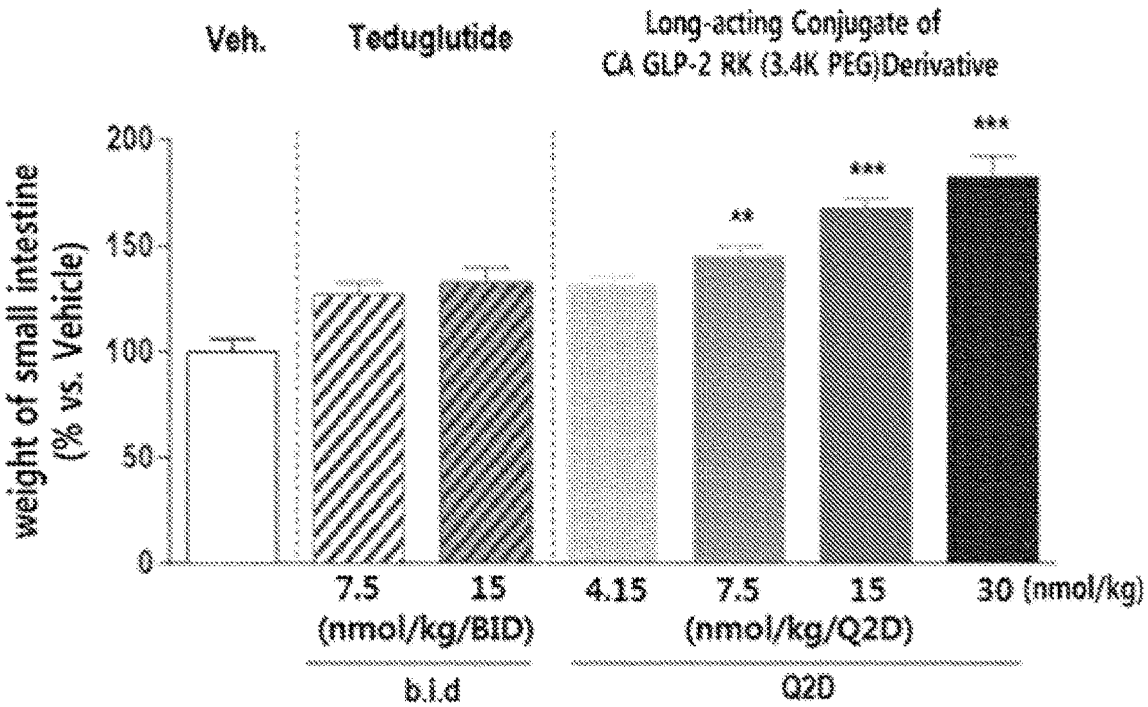
[Fig. 4(B)]
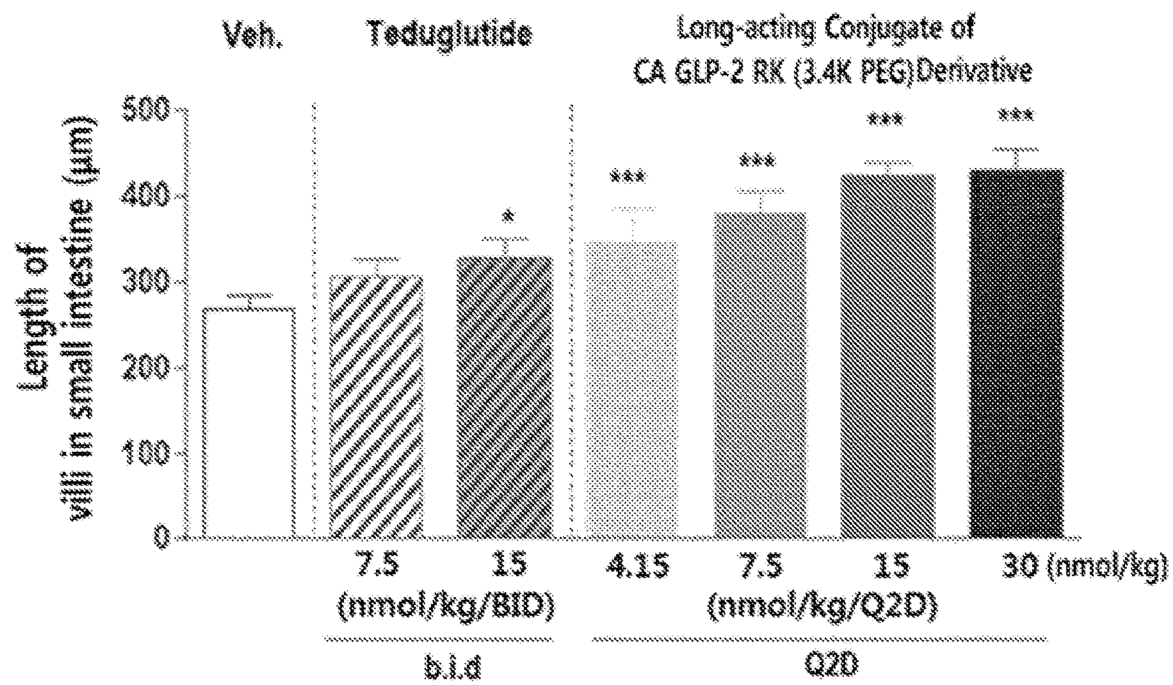

LONG-ACTING CONJUGATES OF GLP-2 DERIVATIVES

CROSS REFERENCE TO RELATED APPLICATIONS

This application is a Divisional application of U.S. application Ser. No. 16/832,634 filed Mar. 27, 2020, which is a bypass continuation application of International Application No. PCT/KR2018/011586 filed Sep. 28, 2018, claiming priority based on Korean Patent Application No. 10-2017-016577, filed Sep. 28, 2017, of which the entire contents are incorporated by reference herein.

SEQUENCE LISTING

The content of the electronically submitted sequence listing, file name: Sequence_Listing_As_Filed.txt; size: 5,257 bytes; and date of creation: Apr. 14, 2022, filed herewith, is incorporated herein by reference in its entirety.

TECHNICAL FIELD

The present invention relates to a glucagon-like peptide-2 (GLP-2) derivative, a conjugate thereof, and a use thereof. In addition, the present invention relates to a method for preparing a glucagon-like peptide-2 (GLP-2) derivative and a conjugate thereof.

BACKGROUND ART

Glucagon-like peptide-2 (GLP-2) is a 33 amino acid peptide hormone which is produced by the intestinal endocrine L cell upon nutrient ingestion. GLP-2 stimulates mucosal growth in the small and large intestines and suppresses growth promotion and apoptosis of intestinal cells and crypt cells. Furthermore, GLP-2 enhances absorption of nutrients in the small intestine and reduces intestinal permeability. In addition, GLP-2 suppresses gastric emptying and gastric acid secretion, while increasing an intestinal blood flow rate and relaxing intestinal smooth muscle. Since GLP-2 has capabilities to absorb and protect energy and activate the function of intestinal cells, it has demonstrated a high therapeutic potential in various in vivo models of intestinal diseases and injuries.

However, GLP-2 still has limitations in being developed into a commercial drug. Peptides such as GLP-2 can be easily denatured due to low stability, loses activity due to degradation by protease in the body, and are easily removed through the kidney due to their relatively small size. Therefore, in order to maintain optimal blood concentrations and titers of peptide drugs, there is a need to administer the peptide drug more frequently. However, most peptide drugs are administered in various types of injections, and frequent injections are required to maintain the blood concentration of the peptide drug, which causes severe pain in patients. In this regard, there have been many attempts to solve these problems, one of which has developed a method of increasing membrane permeability of a peptide drug, leading to the delivery of the peptide drug to the body by inhalation through an oral or a nasal. However, this method has a limitation of a low delivery efficiency of the peptide drug as compared with the injection thereof, and thus it still remains difficult to retain sufficient biological activity of the peptide drug for therapeutic use.

In particular, GLP-2 has extremely short in vivo half-life (7 minutes or shorter) due to its inactivation by dipeptidyl peptidase-IV (DPP IV) which cleaves between the amino acids at position 2 (Ala) and position 3 (Asp) of GLP-2 (Bolette H. et al., The Journal of Clinical Endocrinology & Metabolism. 85(8): 2884-2888, 2000). Attempts have been made to increase the in vivo half-life of GLP-2 mainly through amino acid substitution.

DISCLOSURE

Technical Problem

An object of the present invention is to provide a GLP-2 derivative.

Another object of the present invention is to provide an isolated nucleic acid encoding the GLP-2 derivative, a recombinant expression vector including the same, and a transformant including the recombinant expression vector.

Still another object of the present invention is to provide a method for preparing the GLP-2 derivative.

Still another object of the present invention is to provide a GLP-2 conjugate wherein the GLP-2 derivative and a material capable of increasing its in vivo half-life are linked.

Still another object of the present invention is to provide a method for preparing the GLP-2 conjugate.

Still another object of the present invention is to provide a long-acting formulation of GLP-2 having increased in vivo durability and stability, wherein the long-acting formulation includes the GLP-2 conjugate.

Still another object of the present invention is to provide a pharmaceutical composition for preventing or treating one or more diseases selected from intestinal disease, intestinal injury, and gastrosia, comprising the GLP-2 derivative and/or the GLP-2 conjugate.

Still another object of the present invention is to provide a method for preventing or treating one or more diseases selected from intestinal disease, intestinal injury, and gastrosia, comprising administering the GLP-2 derivative, the GLP-2 conjugate, or the pharmaceutical composition containing the same as an active ingredient to a subject in need thereof.

Still another object of the present invention is to provide a use of the GLP-2 derivative or the GLP-2 conjugate for the preparation of a medicament.

Still another object of the present invention is to provide a use of the GLP-2 derivative or the GLP-2 conjugate for preventing or treating one or more diseases selected from intestinal disease, intestinal injury, and gastrosia.

Technical Solution

In one aspect, the present invention provides a glucagon-like peptide-2 (GLP-2) conjugate, wherein a GLP-2 derivative and an immunoglobulin Fc region are each covalently linked via a non-peptidyl polymer at both termini of the non-peptidyl polymer, and wherein the non-peptidyl polymer is selected from the group consisting of polyethylene glycol, polypropylene glycol, ethylene glycol-propylene glycol copolymer, polyoxyethylated polyol, polyvinyl alcohol, polysaccharide, dextran, polyvinyl ethyl ether, lipid polymer, chitin, hyaluronic acid, and a combination thereof.

In one specific embodiment, the present invention provides the GLP-2 conjugate, wherein the GLP-2 derivative comprises an amino acid sequence of the following General Formula 1:

```
[General Formula 1]
                                  (SEQ ID NO: 9)
X1X2DGSFSDEMNTILDNLAARDFINWLIQTX30ITDX34,
```

wherein, in the above formula, $X_1$ is histidine, imidazoacetyldeshistidine, desaminohistidine, β-hydroxyimidazopropionyldeshistidine, N-dimethylhistidine, or β-carboxyimidazopropionyldeshistidine;

$X_2$ is alanine, glycine, or 2-aminoisobutyric acid (Aib);

$X_{30}$ is lysine or arginine; and $X_{34}$ is absent, or lysine, arginine, glutamine, histidine, 6-azido-lysine, or cysteine; with the proviso that any sequence identical to an amino acid sequence of SEQ ID NO: 1 in General Formula 1 is excluded.

In another specific embodiment, the present invention provides the GLP-2 conjugate, wherein in the General Formula 1 of the GLP-2 derivative, (1) $X_2$ is glycine, (2) $X_{30}$ is arginine, or (3) $X_2$ is glycine and $X_{30}$ is arginine.

In still another specific embodiment, the present invention provides the GLP-2 conjugate, wherein (1) $X_1$ is imidazoacetyldeshistidine, $X_2$ is glycine, $X_{30}$ is lysine, and $X_{34}$ is cysteine;

(2) $X_1$ is imidazoacetyldeshistidine, $X_2$ is glycine, $X_{30}$ is lysine, and $X_{34}$ is lysine;

(3) $X_1$ is imidazoacetyldeshistidine, $X_2$ is glycine, $X_{30}$ is arginine, and $X_{34}$ is lysine;

(4) $X_1$ is imidazoacetyldeshistidine, $X_2$ is glycine, $X_{30}$ is lysine, and $X_{34}$ is 6-azido-lysine;

(5) $X_1$ is imidazoacetyldeshistidine, $X_2$ is glycine, $X_{30}$ is arginine, and $X_{34}$ is cysteine;

(6) $X_1$ is imidazoacetyldeshistidine, $X_2$ is Aib, $X_{30}$ is lysine, and $X_{34}$ is cysteine; or (7) $X_1$ is histidine, $X_2$ is Aib, $X_{30}$ is lysine, and $X_{34}$ is cysteine.

In still another specific embodiment, the present invention provides the GLP-2 conjugate, wherein at least one residue of the GLP-2 derivative is cysteine, lysine, arginine, glutamine, histidine, or 6-azido-lysine.

In still another specific embodiment, the present invention provides the GLP-2 conjugate, wherein the GLP-2 derivative is an amino acid sequence selected from the group consisting of SEQ ID NOS: 2 to 8.

In still another specific embodiment, the present invention provides the GLP-2 conjugate, wherein one end of the non-peptidyl polymer is conjugated to the immunoglobulin Fc region and the other end thereof is conjugated to the hydroxyl group, thiol group, amino group, or azide group of the GLP-2 derivative.

In still another specific embodiment, the present invention provides the GLP-2 conjugate, wherein the immunoglobulin Fc region is non-glycosylated.

In still another specific embodiment, the present invention provides the GLP-2 conjugate, wherein the immunoglobulin Fc region further comprises a hinge region.

In still another specific embodiment, the present invention provides the GLP-2 conjugate, wherein the immunoglobulin Fc region is an IgG4 Fc region.

In another aspect, the present invention provides a GLP-2 derivative comprising an amino acid sequence of the following General Formula 1:

```
[General Formula 1]
                                  (SEQ ID NO: 9)
X1X2DGSFSDEMNTILDNLAARDFINWLIQTX30ITDX34,
```

wherein, in the above formula, $X_1$ is histidine, imidazoacetyldeshistidine, desaminohistidine, β-hydroxyimidazopropionyldeshistidine, N-dimethylhistidine, or β-carboxyimidazopropionyldeshistidine;

$X_2$ is alanine, glycine, or 2-aminoisobutyric acid (Aib);

$X_{30}$ is lysine or arginine; and $X_{34}$ is absent, or lysine, arginine, glutamine, histidine, 6-azido-lysine, or cysteine; with the proviso that any sequence identical to an amino acid sequence of SEQ ID NO: 1 in General Formula 1 is excluded.

In still another specific embodiment, the present invention provides the GLP-2 derivative, wherein in General Formula (1), $X_2$ is glycine, (2) $X_{30}$ is arginine, or (3) $X_2$ is glycine and $X_{30}$ is arginine.

In still another specific embodiment, the present invention provides the GLP-2 derivative, wherein (1) $X_1$ is imidazoacetyldeshistidine, $X_2$ is glycine, $X_{30}$ is lysine, and $X_{34}$ is cysteine;

(2) $X_1$ is imidazoacetyldeshistidine, $X_2$ is glycine, $X_{30}$ is lysine, and $X_{34}$ is lysine;

(3) $X_1$ is imidazoacetyldeshistidine, $X_2$ is glycine, $X_{30}$ is arginine, and $X_{34}$ is lysine;

(4) $X_1$ is imidazoacetyldeshistidine, $X_2$ is glycine, $X_{30}$ is lysine, and $X_{34}$ is 6-azido-lysine;

(5) $X_1$ is imidazoacetyldeshistidine, $X_2$ is glycine, $X_{30}$ is arginine, and $X_{34}$ is cysteine;

(6) $X_1$ is imidazoacetyldeshistidine, $X_2$ is Aib, $X_{30}$ is lysine, and $X_{34}$ is cysteine; or (7) $X_1$ is histidine, $X_2$ is Aib, $X_{30}$ is lysine, and $X_{34}$ is cysteine.

In still another aspect, the present invention provides an isolated nucleic acid encoding the GLP-2 derivative.

In still another aspect, the present invention provides a recombinant expression vector comprising the nucleic acid.

In still another aspect, the present invention provides a transformant comprising the recombinant expression vector.

In still another aspect, the present invention provides a method for preparing the GLP-2 derivative, comprising:

a) culturing a transformant comprising a nucleic acid encoding the GLP-2 derivative to express the GLP-2 derivative; and b) isolating and purifying the expressed GLP-2 derivative.

In still another aspect, the present invention provides a method for preparing a GLP-2 conjugate, comprising:

(a) preparing a complex by reacting a non-peptidyl polymer having two or more terminal reactive groups with one of the GLP-2 derivative and an immunoglobulin Fc region such that the complex has the GLP-2 derivative or the immunoglobulin Fc region attached to one terminal end of the non-peptidyl polymer, and a reactive group at the other terminal end; and (b) preparing a conjugate by reacting the complex prepared in Step (a) with one of the immunoglobulin Fc region and the GLP-2 derivative not attached to the complex such that the GLP-2 derivative and the immunoglobulin Fc region are linked via a non-peptidyl polymer.

In still another specific embodiment, the present invention provides the preparation method, wherein the non-peptidyl polymer comprises one or more reactive groups selected from the group consisting of an aldehyde group, a propionaldehyde group, a butyraldehyde group, a maleimide group, and a succinimide derivative.

In still another specific embodiment, the present invention provides the preparation method, wherein the succinimide derivative is succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

In still another aspect, the present invention provides a long-acting formulation of GLP-2 having increased in vivo durability and stability, wherein the long-acting formulation comprises the GLP-2 conjugate.

In still another aspect, the present invention provides a pharmaceutical composition for preventing or treating one or more diseases selected from intestinal disease, intestinal injury, and gastrosia, comprising the GLP-2 conjugate or the GLP-2 derivative.

In still another embodiment, the present invention provides the pharmaceutical composition, wherein the intestinal disease is short-bowel syndrome, hypersensitive intestinal disease, inflammatory intestinal disease, Crohn's disease, colonitis, colitis, pancreatitis, ileitis, mucositis, or intestine atrophy.

In still another embodiment, the present invention provides the pharmaceutical composition, wherein the gastrosia is stomach cramps, gastritis, gastric ulcer, duodenitis, or duodenal ulcer.

In still another aspect, the present invention provides a method for preventing or treating one or more diseases selected from intestinal disease, intestinal injury, and gastrosia, comprising administering the GLP-2 conjugate, the GLP-2 derivative, or the pharmaceutical composition comprising the same as active ingredients to a subject in need thereof.

In still another aspect, the present invention provides a use of the GLP-2 derivative or the GLP-2 conjugate for the preparation of a medicament.

In still specific embodiment, the present invention provides the use of the GLP-2 derivative or the GLP-2 conjugate, wherein the medicament is used for preventing or treating one or more diseases selected from intestinal disease, intestinal injury, and gastrosia.

In still another aspect, the present invention provides a use of the GLP-2 derivative or the GLP-2 conjugate for the prevention or treatment of one or more diseases selected from intestinal disease, intestinal injury, and gastrosia.

Advantageous Effects

Since the GLP-2 derivative and long-acting conjugate thereof of the present invention have a significantly high activity and a superior in vivo duration effect, these can be effectively used for the prevention, amelioration, and treatment of intestinal disease, intestinal injury, and gastrosia.

BRIEF DESCRIPTION OF THE DRAWINGS

FIG. 1 shows the results in which the purity of the long-acting conjugates of GLP-2 derivatives is analyzed by a reversed-phase column.

FIG. 2 is a graph showing changes in blood concentration of the long-acting conjugates of GLP-2 derivatives.

FIG. 3 is a graph showing changes in blood concentration of Teduglutide and the long-acting conjugate of GLP-2 derivative.

FIG. 4(A) and FIG. 4(B) are graphs showing in vivo effects (FIG. 4(A): weight of small intestine, FIG. 4(B): length of small intestine villi) of the Teduglutide and the long-acting conjugate of GLP-2 derivative.

BEST MODE

The specific details of the present invention will be described as follows. In particular, the explanations and embodiments disclosed in the present invention may be applied to other explanations and embodiments, respectively. That is, all combinations of various elements disclosed in the present invention belong to the scope of the present invention. Furthermore, the scope of the present invention should not be limited by the specific disclosure provided hereinbelow.

Additionally, those skilled in the art will be able to recognize or confirm, based on routine experimentation, many equivalents to the specific embodiments of the present invention described in this application, and such equivalents are intended to be included in the present invention.

Throughout the entire specification, not only the conventional one-letter or three-letter codes for naturally occurring amino acids, but also those three-letter codes generally allowed for other amino acids are used, such as Aib(2-aminoisobutyric acid), $_{AZ}$K(6-azidolysine), etc. Additionally, the amino acids mentioned in abbreviations herein are described according to the IUPAC-IUB rules as follows:

Alanine Ala, A;
Arginine Arg, R;
Asparagine Asn, N;
Aspartic acid Asp, D;
Cysteine Cys, C;
Glutamic acid Glu, E;
Glutamine Gln, Q;
Glycine Gly, G;
Histidine His, H;
Isoleucine Ile, I;
Leucine Leu, L;
Lysine Lys, K;
Methionine Met, M;
Phenylalanine Phe, F;
Proline Pro, P;
Serine Ser, S;
Threonine Thr, T;
Tryptophan Trp, W;
Tyrosine Tyr, Y;
Valine Val, V.

In one aspect, the present invention provides a GLP-2 derivative.

In the present invention, "the GLP-2 derivative" includes a peptide having one or more amino acid sequence differences compared to native GLP-2; a peptide modified through a modification of native GLP-2 sequences; and a mimetic of native GLP-2 having a function of preventing, treating, and/or ameliorating intestinal disease, intestinal injury, and gastrosia as in native GLP-2. In addition, the derivative of GLP-2 also includes a derivative having an excellent activity in vitro and/or in vivo for a GLP-2 receptor.

As used herein, the term "glucagon-like peptide-2 (GLP-2)" refers to a peptide having a function of preventing, treating, and/or ameliorating intestinal disease, intestinal injury, and gastrosia, and it includes not only a native form of GLP-2 but also its agonist, fragments, variants, derivatives, and the like.

As used herein, the term "GLP-2 agonist" refers to a material which can bind to a GLP-2 receptor and induce the same or similar physiological activity as native GLP-2 regardless of its structural similarity to GLP-2.

As used herein, the term "GLP-2 fragment" refers to a peptide having one or more amino acids added to or deleted from the N-terminus or C-terminus of GLP-2, wherein the added amino acid can be a non-naturally occurring amino acid (e.g., D-amino acid).

As used herein, the term "GLP-2 variant" refers to a peptide having one or more amino acids different from native GLP-2. For this, the substitution with a non-naturally occurring amino acid as well as a naturally occurring amino acid can be induced.

In the present invention, the modification for preparing agonists, fragments, variants, and derivatives of native GLP-2 may include all of the modifications using L-type or D-type amino acids and/or non-native amino acids; and/or a modification of native sequence or a post-translational modification (e.g., methylation, acylation, ubiquitination, intramolecular covalent bonding, etc.).

Such agonists, fragments, variants, and derivatives of native GLP-2 may have a function of preventing, treating, and ameliorating intestinal disease, intestinal injury, and gastrosia.

The agonists, fragments, variants, and derivatives of native GLP-2 that are applicable to the present invention can be prepared by a combination of several methods for preparing agonists, fragments, variants, and derivatives.

The GLP-2 used in the present invention can be synthesized by a solid-phase synthesis method, and can also be produced by a recombinant method.

In a specific embodiment, the derivative of GLP-2 may be one that is prepared by any one method of substitution, addition, deletion, and modification of some amino acids of native GLP-2 or by a combination thereof.

The amino acid sequence of native GLP-2 is as follows:

```
GLP-2 (1-33)
                                        (SEQ ID NO: 1)
HADGSFSDEMNTILDNLAARDFINWLIQTKITD
```

Specifically, the GLP-2 derivative comprises a substitution of alanine at the 2nd amino acid of native GLP-2 with glycine or Aib(2-aminoisobutyric acid), a substitution of lysine at the 30th amino acid of native GLP-2 with arginine, or a combination thereof, but is not limited thereto.

Specifically, the GLP-2 derivative may be one which shows a sequence homology of at least 80%, 85%, 90%, 95%, 96%, 97%, 98%, and 99% in the amino acid sequence compared to native GLP-2, and/or is in the form where some groups of an amino acid residue of GLP-2 are altered by chemical substitution (e.g., alpha-methylation, alpha-hydroxylation), deletion (e.g., deamination), or modification (e.g., N-methylation), but the sequence homology and the form of the derivative are not limited thereto.

Specifically, the GLP-2 derivative may be in the form in which a thiol group, an amino group, or an azide group is introduced, but is not limited thereto. Since the GLP-2 derivative has an excellent activity in vitro and/or in vivo for a GLP-2 receptor, and since the conjugation occurs in the introduced group when preparing the long-acting conjugate of GLP-2 derivative, these may be used to prepare a GLP-2 conjugate, the binding site of which is selectively controlled.

Specifically, the hydroxyl group, thiol group, amino group, or azide group of the GLP-2 derivative may be conjugated to one end of a non-peptidyl polymer, and a material (e.g., an immunoglobulin Fc region) capable of increasing the in vivo half-life may be conjugated to the other end of the non-peptidyl polymer. The thiol group, amino group, or azide group may be introduced by adding an amino acid to GLP-2, but is not limited thereto. The thiol group may be introduced by adding cysteine (C) to GLP-2, the amino group may be introduced by adding lysine (K), arginine (R), glutamine (Q), or histidine (H) to GLP-2, and the azide group may be introduced by adding 6-azido-lysine ($_{AZ}$K) to GLP-2, but these are not limited thereto.

Specifically, in the GLP-2 derivative, at least one of the residues may be cysteine, lysine, arginine, glutamine, histidine or 6-azido-lysine, but is not limited thereto.

In another specific embodiment, in the GLP-2 derivative, the N-terminal amino group may be substituted, removed, or modified, but is not limited thereto. In order to prevent binding at the N-terminal end, which is an import site for an in vivo activity of the GLP-2 derivative, when preparing the long-acting conjugate, the GLP-2 derivative of the present invention may be prepared by a method of removing an alpha-amino group of the N-terminal histidine, a method of a substituting N-terminal amino group with a hydroxyl group or a carboxyl group, a method of removing an α-carbon of the N-terminal histidine and a N-terminal amino group conjugated to the α-carbon such that only an imidazoacetyl group remains, and a method of modifying a N-terminal amino group with two methyl groups.

Specifically, the GLP-2 derivative may be an imidazoacetyl-deshistidyl-GLP-2 (CA-GLP-2) prepared by removing an α-carbon of a histidine residue, which is the first amino acid at the N-terminus of the GLP-2, and a N-terminal amino group bound thereto; a des-amino-histidyl GLP-2 (DA-GLP-2) prepared by deleting a N-terminal amino group of the GLP-2; a β-hydroxyimidazopropionyldeshistidyl GLP-2 (HY-GLP-2) prepared by substituting a N-terminal amino group of the GLP-2 with a hydroxyl group; a N-dimethyl-histidyl GLP-2 (DM-GLP-2) prepared by modifying a N-terminal amino group of the GLP-2 with two dimethyl groups; or a β-carboxyimidazopropionyl-deshistidyl-GLP-2 (CX-GLP-2) prepared by substituting a N-terminal amino group of the GLP-2 with a carboxyl group; but is not limited thereto.

Specifically, the GLP-2 derivative of the present invention may comprise the substitution of alanine, which is the 2$^{nd}$ amino acid of native GLP-2, with glycine and the introduction of a thiol group (for example, cysteine) into the C-terminus of the GLP-2; and more specifically, the GLP-2 derivative may comprise imidazoacetyldeshistidine in which an α-carbon of a histidine residue, which is the first amino acid at the N-terminus of the GLP-2, and the N-terminal amino group bound to the α-carbon are removed (for example, it may have an amino acid sequence of SEQ ID NO: 2), but is not limited thereto.

Specifically, the GLP-2 derivative of the present invention may comprise the substitution of alanine, which is the 2$^{nd}$ amino acid of native GLP-2, with glycine, and the introduction of an amino group (e.g., lysine) into the C-terminus; and more specifically, the GLP-2 derivative may comprise imidazoacetyldeshistidine in which an α-carbon of a histidine residue, which is the first amino acid at the N-terminus of the GLP-2, and the N-terminal amino group bound to the α-carbon are removed (for example, it may have an amino acid sequence of SEQ ID NO: 3), but is not limited thereto.

Specifically, the GLP-2 derivative of the present invention may comprise the substitution of alanine, which is the 2$^{nd}$ amino acid of native GLP-2, with glycine, the substitution of lysine, which is the 30$^{th}$ amino acid of native GLP-2, with arginine, and the introduction of an amino group (e.g., lysine) into the C-terminus; and more specifically, the GLP-2 derivative may comprise imidazoacetyldeshistidine in which an α-carbon of a histidine residue, which is the first amino acid at the N-terminus of the GLP-2, and the N-terminal amino group bound to the α-carbon are removed (for example, it may have an amino acid sequence of SEQ ID NO: 4), but is not limited thereto.

Specifically, the GLP-2 derivative of the present invention may comprise the substitution of alanine, which is the $2^{nd}$ amino acid of native GLP-2, with glycine, and the introduction of an azide group (e.g., 6-azido-lysine) into the C-terminus; and more specifically, the GLP-2 derivative may comprise imidazoacetyldeshistidine in which an α-carbon of a histidine residue, which is the first amino acid at the N-terminus of the GLP-2, and the N-terminal amino group bound to the α-carbon are removed (for example, it may have an amino acid sequence of SEQ ID NO: 5), but is not limited thereto.

Specifically, the GLP-2 derivative of the present invention may comprise the substitution of alanine, which is the $2^{nd}$ amino acid of native GLP-2, with glycine, the substitution of lysine, which is the $30^{th}$ amino acid of native GLP-2, with arginine, and the introduction of a thiol group (e.g., cysteine) into the C-terminus; and more specifically, the GLP-2 derivative may comprise imidazoacetyldeshistidine in which an α-carbon of a histidine residue, which is the first amino acid at the N-terminus of the GLP-2, and the N-terminal amino group bound to the α-carbon are removed (for example, it may have an amino acid sequence of SEQ ID NO: 6), but is not limited thereto.

Specifically, the GLP-2 derivative of the present invention may comprise the substitution of alanine, which is the $2^{nd}$ amino acid of native GLP-2, with glycine, and the introduction of a thiol group (e.g., cysteine) into the C-terminus (for example, it may have an amino acid sequence of SEQ ID NO: 8); and more specifically, the GLP-2 derivative may comprise imidazoacetyldeshistidine in which an α-carbon of a histidine residue, which is the first amino acid at the N-terminus of the GLP-2, and the N-terminal amino group bound to the α-carbon are removed (for example, it may have an amino acid sequence of SEQ ID NO: 7), but is not limited thereto.

The GLP-2 derivatives of SEQ ID NOS: 2 to 8 are shown in Table 1 below.

TABLE 1

| Name | Sequence | SEQ ID NO: |
|---|---|---|
| CA GLP-2 KC | *ca*HGDGSFSDEMNTILDNLAARDFINWLIQTKITDC | 2 |
| CA GLP-2 KK | *ca*HGDGSFSDEMNTILDNLAARDFINWLIQTKITDK | 3 |
| CA GLP-2 RK | *ca*HGDGSFSDEMNTILDNLAARDFINWLIQTRITDK | 4 |
| CA GLP-2 $K_{AZ}K$ | *ca*tIGDGSFSDEMNTILDNLAARDFINVVLIQTKITDAzK | 5 |
| CA GLP-2 RC | *ca*FIGDGSFSDEMNTILDNLAARDFINWLIQTRITDC | 6 |
| CA GLP-2 Aib | *ca*HAibDGSFSDEMNTILDNLAARDFINWLIQTKITDC | 7 |
| GLP-2 Aib | HAibDGSFSDEMNTILDNLAARDFINWLIQTKITDC | 8 |

In Table 1 above, $_{ca}$H indicates one that is substituted with imidazoacetyldeshistidine, instead of histidine; Aib indicates 2-aminoisobutyric acid; and $_{AZ}$K indicates 6-azido-L-lysine.

The GLP-2 derivatives according to the present invention may be peptides comprising the specific sequences above, or may be peptides consisting (essentially) of the specific sequences above, but the GLP-2 derivatives are not limited thereto.

Meanwhile, although described as a peptide or a GLP-2 derivative "consisting of a particular SEQ ID NO" in the present invention, such expression does not exclude a mutation in the peptide or the GLP-2 derivative that can occur by a meaningless sequence addition upstream or downstream of the amino acid sequence of the corresponding SEQ ID NO, or a naturally occurring mutation therein, or a silent mutation therein, as long as the peptide or GLP-2 derivative having such mutation has an activity the same as or corresponding to the peptide or GLP-2 derivative which consists of an amino acid sequence of the corresponding SEQ ID NO. Even when the sequence addition or a mutation is present, it obviously belongs to the scope of the present invention.

In still another specific embodiment, the GLP-2 derivative may include an amino acid sequence of the following General Formula 1, but is not limited thereto:

[General Formula 1]

(SEQ ID NO: 9)

$X_1X_2$DGSFSDEMNTILDNLAARDFINWLIQT$X_{30}$ITD$X_{34}$ wherein, in the above formula, $X_1$ is histidine, imidazoacetyldeshistidine, desaminohistidine, β-hydroxyimidazopropionyldeshistidine, N-dimethylhistidine, or β-carboxyimidazopropionyldeshistidine;

$X_2$ is alanine, glycine, or 2-aminoisobutyric acid (Aib);

$X_{30}$ is lysine or arginine; and $X_{34}$ is absent, or lysine, arginine, glutamine, histidine, 6-azido-lysine, or cysteine; with the proviso that any sequence identical to an amino acid sequence of SEQ ID NO: 1 in General Formula 1 is excluded.

Specifically, in General Formula 1, (1) $X_2$ may be glycine, (2) $X_{30}$ may be arginine, or (3) $X_2$ may be glycine and $X_{30}$ may be arginine, but these are not limited thereto.

Specifically, in General Formula 1, (1) $X_1$ may be imidazoacetyldeshistidine, $X_2$ may be glycine, $X_{30}$ may be lysine, and $X_{34}$ may be cysteine;

(2) $X_1$ may be imidazoacetyldeshistidine, $X_2$ may be glycine, $X_{30}$ may be lysine, and $X_{34}$ may be lysine;

(3) $X_1$ may be imidazoacetyldeshistidine, $X_2$ may be glycine, $X_{30}$ may be arginine, and $X_{34}$ may be lysine;

(4) $X_1$ may be imidazoacetyldeshistidine, $X_2$ may be glycine, $X_{30}$ may be lysine, and $X_{34}$ may be 6-azido-lysine;

(5) $X_1$ may be imidazoacetyldeshistidine, $X_2$ may be glycine, $X_{30}$ may be arginine, and $X_{34}$ may be cysteine;

(6) $X_1$ may be imidazoacetyldeshistidine, $X_2$ may be Aib, $X_{30}$ may be lysine, and $X_{34}$ may be cysteine; or (7) $X_1$ may be histidine, $X_2$ may be Aib, $X_{30}$ may be lysine, and $X_{34}$ may be cysteine, but these are not limited thereto.

Meanwhile, the GLP-2 derivative may include all of those in the form of the peptide itself, a salt thereof (e.g., a pharmaceutically acceptable salt of the peptide), or a solvate thereof.

Additionally, the peptide or the GLP-2 derivative may be in any pharmaceutically acceptable form.

The kind of the salt is not particularly limited. However, the salt is preferably one that is safe and effective to a subject, e.g., a mammal, but is not particularly limited thereto.

The term "pharmaceutically acceptable" refers to a material which can be effectively used for the intended use within the scope of pharmaco-medical decision without inducing excessive toxicity, irritation, allergic responses, etc.

As used herein, the term "pharmaceutically acceptable salt" refers to a salt derived from pharmaceutically acceptable inorganic acids, organic acids, or bases. Examples of the suitable salts may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Examples of the salts derived from suitable bases may include alkali metals such as sodium, potassium, etc.; alkali earth metals such as magnesium; ammonium, etc.

Additionally, as used herein, the term "solvate" refers to a complex formed between the peptide according to the present invention or a salt thereof and a solvent molecule.

The GLP-2 derivative of the present invention may be synthesized by a solid phase synthesis method, can also be produced by a recombinant method, and can be produced commercially.

In another aspect, the present invention provides an isolated nucleic acid encoding the GLP-2 derivative, a recombinant expression vector including the nucleic acid, and a transformant including the recombinant expression vector.

The GLP-2 derivative is as described above.

As used herein, the term "nucleic acid" refers to a deoxyribonucleotide (DNA) or a ribonucleotide (RNA), existing in a single- or double-stranded form, including genomic DNA, cDNA, and RNA transcribed therefrom, and a nucleotide as the basic constituting unit not only includes natural nucleotides but also includes analogues having modifications in a sugar or base (Scheit, Nucleotide Analogs, John Wiley, New York, 1980; Uhlman and Peyman, Chemical Reviews, 90: 543-584, 1990). The nucleic acid of the present invention may be isolated or prepared using standard technology in molecular biology. For example, the nucleic acid can be amplified by PCR (polymerase chain reaction) from native GLP-2 gene sequences using appropriate primer sequences, and can be prepared using standard synthetic techniques using an automated DNA synthesizer.

As used herein, the term "vector" refers to a recombinant vector capable of expressing a target protein in an appropriate host cell, which is a nucleic acid construct including essential regulatory factors operably linked to enable the expression of a nucleic acid insert. In the present invention, a recombinant vector can be prepared, which includes a nucleic acid encoding a GLP-2 derivative. In addition, the GLP-2 derivative of the present invention may be obtained via transformation or transfection of the recombinant vector into a host cell.

The recombinant vector according to the present invention may typically be constructed as a vector for cloning or as a vector for expression, and also can be constructed using a prokaryotic or eukaryotic cell as a host cell.

In the present invention, the nucleic acid encoding the GLP-2 derivative is operably linked to a promoter.

As used herein, the term "operably linked" refers to a functional connection between a regulatory sequence for nucleic acid expression (e.g., a promoter, a signal sequence, a ribosome-binding site, a transcription termination sequence, etc.) and a different nucleic acid sequence, and the regulatory sequence can regulate the transcription and/or translation of the different nucleic acid sequence.

As used herein, the term "promoter" refers to an untranslated nucleic acid sequence located upstream of a coding region, which includes a polymerase-binding site and has the activity of initiating transcription of a gene located downstream of a promoter into mRNA, i.e., a DNA domain to which polymerase binds and initiates the transcription of a gene, and it may be located at the 5' domain of an mRNA transcription initiation site.

For example, when the vector of the present invention is a recombinant vector and uses a prokaryotic cell as a host cell, a strong promoter (e.g., tac promoter, lac promoter, lacUV5 promoter, 1pp promoter, pLλ promoter, pRλ promoter, rac5 promoter, amp promoter, recA promoter, SP6 promoter, trp promoter, T7 promoter, etc.) capable of executing transcription, a ribosome-biding site for the initiation of translation, and transcription/translation termination sequences should be included.

Additionally, the vector to be used in the present invention may be prepared by manipulating the plasmids (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series, pPICZα series, pUC19, etc.), phages (e.g., λgt4·λB, λ-Charon, λΔz1, M13, etc.), or viruses (e.g., SV40, etc.) which are commonly used in the art.

Meanwhile, when the vector of the present invention is a recombinant vector and uses a eukaryotic cell as a host cell, promoters derived from the genomes of mammalian cells (e.g., metallothionein promoter) or promoters derived from the mammalian viruses (e.g., adenovirus late promoter, 7.5K promoter of papillomavirus, SV40 promoter, cytomegalovirus promoter, and tk promoter of HSV) may be used, and in general, includes a polyadenylated sequence (e.g., bovine growth hormone terminator and a polyadenylated sequence derived from SV40) as a transcription termination sequence.

Additionally, the recombinant vector of the present invention includes an antibiotic-resistance gene commonly used in the art as a selective marker, and may include, for example, genes having resistance to ampicillin, gentamycin, carbenicillin, chloramphenicol, streptomycin, kanamycin, geneticin, neomycin, and tetracycline.

The recombinant vector of the present invention may additionally include a sequence so as to facilitate the purification of the target protein being collected, i.e., a GLP-2 derivative. The sequence to be additionally included may be a tag sequence for protein purification, e.g., glutathione S-transferase (Pharmacia, USA), a maltose-binding protein (NEB, USA), FLAG (IBI, USA), hexahistidine, etc., but the kinds of the sequence necessary for the purification of target proteins are not limited thereto.

Fusion proteins expressed by the recombinant vector including the above tag sequence may be purified by affinity chromatography. For example, when glutathione-S-transferase is fused, glutathione, which is the substrate of the enzyme, may be used, and when 6-histidine tags are used, a target protein may be easily collected by a Ni-NTA column.

As used herein, the term "transformation" refers to a process of introducing DNA into a host cell and making the DNA to be replicable therein as a chromosomal factor or by completion of chromosomal integration, which is a phenomenon of artificially causing a genetic change by introducing exogenous DNA into a cell.

The method of transformation used in the present invention may be any transformation method, and it may be easily performed according to the conventional method used in the art. Examples of the commonly used transformation method may include a $CaCl_2$ precipitation method, a Hanahan method with improved efficiency using dimethyl sulfoxide (DMSO) as a reducing agent in the $CaCl_2$ precipitation method, electroporation, a $CaPO_4$ precipitation method, a protoplast fusion method, a stirring method using silicon carbide fiber, an agrobacteria-mediated transformation, a transformation using PEG, dextran sulfate-, lipofectamine-, and dry/suppression-mediated transformations, etc.

The method for transforming the recombinant vector including a nucleic acid encoding the GLP-2 derivative according to the present invention is not limited to these methods, and any method for transformation or transfection commonly used in the art may be used without limitation.

The transformant of the present invention may be obtained by introducing a recombinant vector including the target nucleic acid which encodes a GLP-2 derivative into a host cell.

An appropriate host to be used in the present invention may not be particularly limited, but any hosts that can express the nucleic acid of the present invention may be used. Examples of the appropriate host may include bacteria belonging to the genus *Escherichia* such as *E. coli*, bacteria belonging to the genus *Bacillus* such as *Bacillus subtilis*, bacteria belonging to the genus *Pseudomonas* such as *Pseudomonas putida*, yeasts such as *Pichia pastoris, Saccharomyces cerevisiae*, and *Schizosaccharomyces pombe*, insect cells such as *Spodoptera frugiperda* (SF9), and animal cells such as CHO, COS, and BSC. Specifically, *E. coli* may be used as a host cell, but is not limited thereto.

In still another aspect, the present invention provides a method for preparing a GLP-2 derivative using the transformant.

Specifically, the present invention provides a method for preparing the GLP-2 derivative, comprising:

a) culturing a transformant including a nucleic acid encoding the GLP-2 derivative to express the GLP-2 derivative; and b) isolating and purifying the expressed GLP-2 derivative.

In the present invention, the medium used in culturing the transformant must meet the requirements for host cell cultivation in an appropriate manner. The carbon sources that may be contained in the medium for the growth of a host cell may be appropriately selected by the decision of those skilled in the art according to the type of the transformant prepared thereof, and appropriate cultivation conditions may be selected so as to control the period and amount of cultivation.

Examples of the sugar source to be used in the medium may include sugars and carbohydrates such as glucose, saccharose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These materials may be used alone or in combination.

Examples of the nitrogen source to be used may include peptone, yeast extract, meat gravy, malt extract, corn steep liquor, soybean flour, and urea, or inorganic compounds such as ammonium sulfate, ammonium chloride, ammonium phosphate, ammonium carbonate, and ammonium nitrate. The nitrogen source may also be used alone or in combination.

Examples of the phosphorous source to be used may include potassium dihydrogen phosphate or dipotassium hydrogen phosphate or a corresponding sodium-containing salt. Additionally, the culture medium may contain a metal salt such as magnesium sulfate or iron sulfate necessary for growth.

Lastly, essential growth materials such as amino acids and vitamins may be used. Additionally, appropriate precursors for a culture medium may also be used. The above sources may be appropriately added to a culture during cultivation by a batch culture or continuous culture. The pH of the culture may be appropriately adjusted using a basic compound such as sodium hydroxide, potassium hydroxide, and ammonia, or an acidic compound such as phosphoric acid or sulfuric acid. Additionally, an antifoaming agent such as fatty acid polyglycol ester may be added to prevent foam generation. Additionally, in order to maintain the aerobic state of the culture, oxygen or an oxygen-containing gas (e.g., air) may be injected into the culture.

The transformant of the present invention may be cultured at 20° C. to 45° C., and specifically at 25° C. to 40° C. Additionally, the cultivation is continued until the maximum amount of production of the desired GLP-2 derivative is obtained, and in this regard, the cultivation may normally be continued for 10 hours to 160 hours.

As described above, the transformant of the present invention can produce the GLP-2 derivative when appropriate culture conditions are provided according to a host cell, and the GLP-2 derivative produced according to the vector constitution and characteristics of a host cell may be secreted within the cytoplasm or into the periplasmic space of the host cell or extracellularly.

The proteins expressed within or outside of the host cell may be purified by a conventional method. Examples of the purification method may include salting-out (e.g., ammonium sulfate precipitation, sodium phosphate precipitation, etc.), solvent precipitation (e.g., protein fraction precipitation using acetone or ethanol, etc.), dialysis, gel filtration, ion exchange, or chromatography such as reversed column chromatography, ultrafiltration, etc., and these methods may be used alone or in combination.

In still another aspect, the present invention provides a formulation that increases the half-life and bioavailability of the GLP-2 derivative, or that continuously maintains its activity. Specifically, the formulation refers to a formulation containing a carrier that directly covalently binds to a GLP-2 derivative, or a formulation containing a component capable of enhancing the maintenance of the in vivo activity of the GLP-2 derivative even when there is no direct covalent bond.

Additionally, in still another aspect, the present invention provides a GLP-2 conjugate in which a GLP-2 derivative and a material capable of increasing the in vivo half-life of the GLP-2 derivative are linked. Additionally, the GLP-2 derivative of the present invention has an activity higher than native GLP-2, and a long-acting conjugate thereof has significantly increased blood half-life. Therefore, the GLP-2 conjugate of the present invention can be effectively used for the prevention, treatment, and/or amelioration of intestinal disease, intestinal injury, or gastrosia.

The GLP-2 derivative is as described above.

In a specific embodiment, in the conjugate of the present invention, the GLP-2 derivative and a material capable of increasing the in vivo half-life of the GLP-2 derivative may be linked through a linker.

In the GLP-2 conjugate of the present invention, a covalent bond is formed between the linker and a thiol group, an amino group, or an azide group, which is introduced into the GLP-2 derivative, and thereby the binding site of the GLP-2 derivative and linker can be selectively adjusted.

Additionally, in the GLP-2 conjugate, the amino group at the N-terminus of the GLP-2 derivative is substituted, deleted, or modified so that the binding of a linker to the N-terminal end, which is an important site for an in vivo activity, is prevented, and thus the binding site of the GLP-2 derivative and linker can be selectively adjusted, but is not limited thereto.

As used herein, the term "material capable of increasing an in vivo half-life" refers to a substance which can be linked to a GLP-2 derivative to thereby prolong the half-life of the GLP-2 derivative. As used herein, the term "material capable of increasing an in vivo half-life" can be interchangeably used with the term "biocompatible material" or "carrier".

The biocompatible material or carrier may include any material as long as it can be linked to the GLP-2 derivative and prolong the half-life of the GLP-2 derivative, for example, those selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, an in vivo connective tissue or a derivative thereof, a nucleotide, fibronectin, transferrin, saccharide, and a polymer, but are not limited thereto.

The biocompatible material or carrier may be linked to the GLP-2 derivative via a covalent or non-covalent bond. Additionally, the method of linking the GLP-2 derivative to the biocompatible material or carrier may include a genetic recombination technique and an in vitro linking using polymers or low-molecular weight chemicals, but is not limited to any specific linking method.

In the present invention, when polyethylene glycol is used as a carrier, the Recode technology by Ambrx, Inc., which enables a position-specific attachment of polyethylene glycol, may be included, and the glycopegylation technology by Neose Technologies, Inc., which enables a specific attachment in the area of glycan, may also be included. Additionally, the method may include a releasable PEG technique, which enables a slow release of polyethylene glycol in the body, but the method is not limited thereto, and technologies capable of increasing in vivo bioavailability using PEG may also be included.

Additionally, one or more polymers, such as polyethylene glycol, polypropylene glycol, ethylene glycol-propylene glycol copolymer, polyoxyethylated polyol, polyvinyl alcohol, polysaccharide, dextran, polyvinyl ethyl ether, biodegradable polymer, lipopolymer, chitin, or hyaluronic acid, can also be linked to the GLP-2 derivative by the technologies above.

In the present invention, when albumin is used as a carrier, a technology capable of increasing in vivo stability by a direct covalent bonding between albumin or an albumin fragment and the GLP-2 derivative may be used. Additionally, instead of directly linking albumin to the GLP-2 derivative, a technology which indirectly allows albumin to be linked to the GLP-2 derivative by linking a material capable of binding to albumin, e.g., an albumin-specific antibody or antibody fragment thereof, to the GLP-2 derivative; a technology of linking a particular peptide/protein having a binding affinity to albumin (e.g., an albumin-binding peptide produced via Albumod technology by Affibody AB) to the GLP-2 derivative; and a technology of linking a fatty acid or the like having a binding affinity to albumin, etc., may be used, but the method is not limited thereto, and any technology or linking method that can improve in vivo stability using albumin may be used without limitation.

In order to increase the in vivo half-life, a technology of binding to the GLP-2 derivative using an antibody or antibody fragment thereof as a carrier may be included within the scope of the present invention. It may be an antibody or antibody fragment thereof including an FcRn-binding region, or any antibody fragment which does not include the FcRn-binding region such as Fab, etc. The CovX-body technology by CovX Research LLC using a catalytic antibody may be included, and a technology increasing an in vivo half-life using the immunoglobulin Fc region may also be included within the scope of the present invention.

The FcRn-binding material may be an immunoglobulin Fc region.

As used herein, the term "immunoglobulin Fc region" refers to a part excluding the variable regions of the heavy and light chains, the heavy-chain constant region 1 (CH1) and the light-chain constant region (CL) of an immunoglobulin, and may further include a hinge region at the heavy-chain constant region. In particular, the immunoglobulin Fc region may be a fragment including a part or all of the immunoglobulin Fc region, and thus may be interchangeably used with the term "immunoglobulin fragment" or "immunoglobulin constant region".

A native Fc has a sugar chain at position Asn297 of heavy-chain constant region 1, but *E. coli*-derived recombinant Fc is expressed as an aglycosylated form. The removal of sugar chains from Fc results in a decrease in a binding affinity of Fc gamma receptors 1, 2, and 3 and complement (c1q) to heavy-chain constant region 1, leading to a decrease or loss in antibody-dependent cell-mediated cytotoxicity or complement-dependent cytotoxicity.

As used herein, the term "immunoglobulin constant region" refers to an immunoglobulin fragment that is devoid of the variable regions of light and heavy chains, the constant region 1 of the heavy chain (CH1), and the constant region of the light chain (CL), that is, an Fc region comprised of the constant regions 2 and 3 of the heavy chain (CH2 and CH3) (or inclusive of the constant region 4 of the heavy chain (CH4)). Optionally, the immunoglobulin Fc region may further comprise a hinge region in the constant region of the heavy chain. In addition, the immunoglobulin constant region of the present invention may be an extended immunoglobulin Fc region which comprises a part or the entirety of the constant region 1 of the heavy chain (CH1) and/or the constant region of the light chain (CL) except for only the variable regions of heavy and light chains of the immunoglobulin so long as it shows effects substantially identical or superior to those of the native immunoglobulin constant region. Further, the immunoglobulin constant region of the present invention may lack a significant part of the amino acid sequence which corresponds to CH2 and/or CH3. Consequently, the immunoglobulin constant region of the present invention may comprise (1) a CH1 domain, a CH2 domain, a CH3 domain, and a CH4 domain, (2) a CH1 domain and a CH2 domain, (3) a CH1 domain and a CH3 domain, (4) a CH2 domain and a CH3 domain, (5) a combination of one or more constant domains and an immunoglobulin hinge region (or a partial hinge region), or (6) a dimer of each constant domain of the heavy chain and the constant region of the light chain. An immunoglobulin constant region including an Fc region is a biodegradable polypeptide which can be metabolized in vivo, such that it can be safely used as a drug carrier. In addition, an immunoglobulin Fc region is more advantageous in terms of production, purification, and production yield of a conjugate than an entire immunoglobulin molecule owing to its relatively low molecular weight. Further, since it is devoid of Fab, which exhibits high non-homogeneity due to the difference in amino acid sequence from one antibody to another, the immunoglobulin Fc alone provides the conjugate with significantly enhanced homogeneity, and reduces the possibility of inducing blood antigenicity.

On the other hand, the immunoglobulin constant region may originate from humans, or animals, such as cows, goats, pigs, mice, rabbits, hamsters, rats, guinea pigs, etc., and may be specifically of human origin. In addition, the immunoglobulin constant region may be selected from constant regions derived from IgG, IgA, IgD, IgE, IgM, or combinations or hybrids thereof. Specifically, the constant region is derived from IgG or IgM, which are the most abundant in blood, and most specifically from IgG, which is known to improve the half-life of ligand-binding proteins. In the present invention, the immunoglobulin Fc region may be a dimer or multimer consisting of single-chain immunoglobulins of domains of the same origin.

As used herein, the term "combination" means that polypeptides encoding single chain immunoglobulin constant regions (preferably Fc regions) of the same origin are linked to a single-chain polypeptide of a different origin to form a dimer or multimer. That is, a dimer or a multimer may be prepared from two or more fragments selected from the group consisting of Fc fragments of IgG Fc, IgA Fc, IgM Fc, IgD Fc, and IgE Fc.

As used herein, the term "hybrid" means that sequences encoding two or more immunoglobulin constant regions of different origins are present in a single chain of an immunoglobulin constant region (preferably, an Fc region). In the present invention, various hybrid forms are possible. For example, the hybrid domain may be composed of one to four domains selected from the group consisting of CH1, CH2, CH3, and CH4 of IgG Fc, IgM Fc, IgA Fc, IgE Fc, and IgD Fc, and may further include a hinge region.

IgG may be divided into the IgG1, IgG2, IgG3, and IgG4 subclasses, and the present invention may include combinations or hybrids thereof. Preferred are the IgG2 and IgG4 subclasses, and most preferred is the Fc region of IgG4, which rarely has effector functions such as complement-dependent cytotoxicity (CDC).

Additionally, the immunoglobulin constant region may have the glycosylated form to the same extent as, or to a greater or lesser extent than the native form or may be the deglycosylated form. Increased or decreased glycosylation or deglycosylation of the immunoglobulin constant region may be achieved by typical methods, for example, by using a chemical method, an enzymatic method, or a genetic engineering method using microorganisms. Herein, when deglycosylated, the complement (Clq) binding to an immunoglobulin constant region becomes significantly decreased and antibody-dependent cytotoxicity or complement-dependent cytotoxicity is reduced or removed, thereby not inducing unnecessary immune responses in vivo. In this context, deglycosylated or aglycosylated immunoglobulin constant regions are more consistent with the purpose of drug carriers. Accordingly, the immunoglobulin Fc region may be more specifically an aglycosylated Fc region derived from human IgG4, that is, a human IgG4-derived aglycosylated Fc region. The human-derived Fc region is more preferable than a non-human derived Fc region, which may act as an antigen in the human body and cause undesirable immune responses such as the production of a new antibody against the antigen.

Further, the immunoglobulin constant region of the present invention includes not only the native amino acid sequence but also sequence derivatives (mutants) thereof. The amino acid sequence derivative means that it has an amino acid sequence different from the wild-type amino acid sequence as a result of deletion, insertion, conserved or non-conserved substitution of one or more amino acid residues, or a combination thereof. For instance, amino acid residues at positions 214 to 238, 297 to 299, 318 to 322, or 327 to 331 in IgG Fc, known to be important for linkage, may be used as the sites suitable for modification. Various derivatives, such as those prepared by removing the sites capable of forming disulfide bonds, removing several N-terminal amino acids from native Fc, or adding methionine to the N-terminus of native Fc, may be used. In addition, complement fixation sites, e.g., C1q fixation sites, or ADCC sites may be eliminated to remove the effector function. The techniques of preparing the sequence derivatives of the immunoglobulin constant region are disclosed in International Patent Publication Nos. WO 97/34631 and WO 96/32478.

Amino acid substitutions in a protein or peptide molecule that do not alter the activity of the molecule are well known in the art (H. Neurath, R. L. Hill, The Proteins, Academic Press, New York, 1979). The most common substitutions occur between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly, in both directions. Optionally, amino acids may be modified by phosphorylation, sulfation, acrylation, glycosylation, methylation, farnesylation, acetylation, amidation, or the like.

The above-described immunoglobulin constant region derivative may be a derivative which has a biological activity equivalent to that of the immunoglobulin constant region of the present invention, but has increased structural stability of the immunoglobulin constant region against heat, pH, etc. Further, the immunoglobulin constant region may be obtained from a native type isolated from humans or animals such as cows, goats, pigs, mice, rabbits, hamsters, rats, guinea pigs, etc., or may be their recombinants or derivatives obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and $F(ab)_2$ fragments. These fragments may be subjected, for example, to size exclusion chromatography to isolate Fc or pF'c.

Specifically, a human-derived immunoglobulin constant region may be a recombinant immunoglobulin constant region that is obtained from a microorganism.

In the present invention, the linker may be bound to the N-terminus, C-terminus, thiol group (e.g., cysteine), amino group (e.g., lysine, arginine, glutamine, or histidine), and/or hydroxyl group of the material capable of increasing an in vivo half-life; and may be bound to the N-terminus, C-terminus, thiol group (e.g., cysteine), amino group (e.g., lysine, arginine, glutamine, or histidine), azide group (e.g., 6-azido-lysine), and/or hydroxyl group of the GLP-2 derivative, but these are not limited thereto.

The linker may be a peptidyl linker or a non-peptidyl linker.

By using a polymer resistant to proteinase as the peptidyl linker, the blood half-life of the GLP-2 derivative can be maintained similarly as in a material capable of increasing the in vivo half-life of the GLP-2 derivative. Therefore, the non-peptidyl linker that can be used in the present invention can be used without limitation as long as it is a non-peptidyl polymer which is resistant to in-vivo proteinase.

As used herein, the term "non-peptidyl polymer" includes a biocompatible polymer in which two or more repeating units are conjugated, and is used interchangeably with the term "non-peptidyl linker". The repeating units are linked to each other through any covalent bond, not a peptide bond. In the present invention, the non-peptidyl polymer includes reactive groups at its ends, and thus a conjugate can be formed by reacting with other components which constitute the conjugate. Such non-peptidyl polymer may have two ends or three ends.

As used herein, the term "non-peptidyl polymer linkage moiety" refers to a constituting element in a conjugate which was formed by linking a non-peptidyl polymer having reactive groups at both ends to an immunoglobulin Fc region and a GLP-2 derivative through each reactive group of the non-peptidyl polymer.

In a specific embodiment of the present invention, the GLP-2 conjugate may be one in which an immunoglobulin Fc region and a GLP-2 derivative are linked together through a non-peptidyl polymer, which includes at both ends reactive groups that can be linked to the immunoglobulin Fc region and GLP-2 derivative.

Specifically, although not particularly limited thereto, the non-peptidyl polymer may be one selected from the group consisting of polyethylene glycol, polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), a lipid polymer, chitins, hyaluronic acid, an oligonucleotide, and a combination thereof. In a more specific embodiment, the non-peptidyl polymer may be polyethylene glycol, but is not limited thereto. Additionally, the derivatives of the above materials already known in the art and the derivatives that can be easily produced at the technology level in the art also belong to the scope of the present invention.

The bonding by the linker may be any chemical bond such as a non-covalent chemical bond or a covalent chemical bond, but is not limited thereto.

The non-peptidyl polymer which can be used in the present invention may be used without limitation as long as it is a polymer resistant to in vivo protease. Specifically, the molecular weight of the non-peptidyl polymer may be in the range of more than 0 kDa to 200 kDa, specifically in the range of 1 kDa to 100 kDa, more specifically in the range of 1 kDa to 50 kDa, further more specifically in the range of 1 kDa to 20 kDa, still further more specifically in the range of 3.4 kDa to 10 kDa, and most specifically about 3.4 kDa, but is not limited thereto.

Additionally, the carrier, especially the non-peptidyl polymer of the present invention, linked to the immunoglobulin Fc region, may be one kind of polymer or a combination of different kinds of polymers.

In one specific embodiment, both ends of the non-peptidyl polymer may be bound to a thiol group, an amino group, or a hydroxyl group of the immunoglobulin Fc region, and may be bound to a thiol group, an amino group, an azide group, or a hydroxyl group of the GLP-2 derivative.

Specifically, the non-peptidyl polymer may include a reactive group capable of binding to each of the immunoglobulin Fc and GLP-2 derivative at both ends. Specifically the reactive group can bind to a thiol group of cysteine; an amino group located at the N-terminus, lysine, arginine, glutamine, and/or histidine; and/or a hydroxyl group located at the C-terminus of the immunoglobulin Fc region, and can bind to thiol group; an amino group of lysine, arginine, glutamine, and/or histidine; an azide group of azido-lysine; and/or a hydroxyl group of the GLP-2 derivative, but the reactive groups are not limited thereto.

More specifically, the reactive group of the non-peptidyl polymer may be one or more selected from the group consisting of an aldehyde group, a propionaldehyde group, butyraldehyde group, a maleimide group, and a succinimide derivative, but is not limited thereto.

In the above, an example of the aldehyde group may be a propionaldehyde group or a butyraldehyde group, but is not limited thereto.

In the above, an example of the succinimide derivative may be succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate, but is not limited thereto.

The non-peptidyl polymer may be linked to the immunoglobulin Fc and GLP-2 derivative through the reactive groups to be converted to a non-peptidyl polymer linker moiety.

Additionally, a final product produced by reductive alkylation via an aldehyde bond is much more stable than one linked by an amide bond. The aldehyde reactive group selectively reacts with the N-terminus at a low pH and may form a covalent bond with a lysine residue at a high pH, for example, pH 9.0.

The terminal reactive groups of the non-peptidyl polymer of the present invention may be the same as or different from each other. The non-peptidyl polymer may have an aldehyde reactive group at both termini. Alternatively, the non-peptidyl polymer may have an aldehyde group and a maleimide group at each terminus, or may have an aldehyde group and a succinimide reactive group at each terminus, but is not limited thereto.

For example, the non-peptidyl polymer may have a maleimide group at one terminus and an aldehyde group, a propionaldehyde group, or a butyraldehyde group at the other terminus. As another example, the non-peptidyl polymer may have a succinimidyl group at one terminus and a propionaldehyde group or butyraldehyde group at the other terminus.

When poly(ethylene glycol) having a hydroxyl group at a propionaldehyde terminus is used as the non-peptidyl polymer, the hydroxyl group may be activated by the various reactive groups by a known chemical reaction, or poly (ethylene glycol) having a commercially available modified reactive functional group may be used to prepare the conjugate of the present invention.

In one specific embodiment, the reactive group of the non-peptidyl polymer may be linked to a cysteine residue of the GLP-2 derivative, specifically to a —SH group of cysteine, but is not limited thereto.

In the case of using maleimide-PEG-aldehyde, the maleimide group may be linked to a —SH group of the GLP-2 derivative by a thioether bond, and the aldehyde group may be linked to a —$NH_2$ group of the immunoglobulin Fc through a reductive alkylation reaction, but the present invention is not limited thereto, and this corresponds to one example.

Through such reductive alkylation, the N-terminal amine group of the immunoglobulin Fc region is linked to the oxygen atom located at one terminus of the PEG through a linker functional group having a structure of —$CH_2CH_2CH_2$— to form a structure of -PEG-O—$CH_2CH_2CH_2NH$-immunoglobulin Fc. In addition, through the thioether bond, a structure in which the one terminus of the PEG is linked to the sulfur atom located in the cysteine of the GLP-2 derivative may be formed. The thioether bond described above may include a structure of

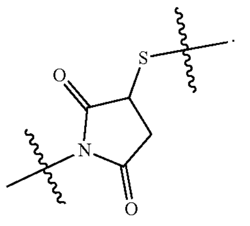 [SMILES: *SC1CC(=O)N(*)C1=O]

However, the present invention is not particularly limited to the above-described example, and this corresponds to one example.

Additionally, in the conjugate, the reactive group of the non-peptidyl polymer may be linked to —$NH_2$ located at the N-terminus of the immunoglobulin Fc region, but this corresponds to one example.

Additionally, in the conjugate, the reactive group of the GLP-2 derivative may be linked to the non-peptidyl polymer having a reactive group through the C-terminus of the GLP-2 derivative, and it corresponds to one example.

As used herein, the term "C-terminus" refers to a carboxy terminus of the peptide, and refers to a position capable of binding with the non-peptidyl polymer for the purpose of the present invention. For example, the C-terminus may include both an amino acid residue at the very end of the C-terminus and an amino acid residue near the C-terminus, and specifically, may include the $1^{st}$ to $20^{th}$ amino acid residues from the very end, although the C-terminus is not limited thereto.

In one specific embodiment, the linkage of a material capable of prolonging the in vivo half life of the GLP-2 derivative may be performed by a genetic recombinant method.

In one specific embodiment, the GLP-2 conjugate of the present invention is a GLP-2 conjugate wherein the GLP-2 derivative and the immunoglobulin Fc region are each covalently linked via a non-peptidyl polymer at both termini of the non-peptidyl polymer.

Herein, the non-peptidyl polymer may be selected from the group consisting of polyethylene glycol, polypropylene glycol, ethylene glycol-propylene glycol copolymer, polyoxyethylated polyol, polyvinyl alcohol, polysaccharide, dextran, polyvinyl ethyl ether, lipid polymer, chitin, hyaluronic acid, or a combination thereof.

Specifically, in the GLP-2 derivative of the present invention, a covalent bond may be formed between the linker, which is the non-peptidyl polymer, and the introduced thiol group, amino group, or azide group. Therefore, when the GLP-2 derivative of the present invention is used, a GLP-2 conjugate can be obtained in which the binding site is selectively adjusted.

Additionally, since in the GLP-2 derivative of the present invention, the N-terminal amino group is substituted, deleted, or modified, the binding of the non-peptidyl polymer to the N-terminus, an important site for an in vivo activity, is prevented, and thereby a GLP-2 conjugate can be obtained in which the binding site is selectively adjusted.

In the present invention, the GLP-2 conjugate is used interchangeably with the term "conjugate of GLP-2 derivative", "long-acting conjugate of GLP-2 derivative", or "long-acting GLP-2 derivative conjugate".

In still another aspect, the present invention provides a method for preparing a GLP-2 conjugate, comprising linking the GLP-2 derivative to a material capable of increasing the in vivo half-life of the GLP-2 derivative.

The GLP-2 derivative, the material capable of increasing the in vivo half-life of the GLP-2 derivative, and the GLP-2 conjugate are as described above.

Specifically, the method may comprise:

(a) preparing a complex by reacting a non-peptidyl polymer having two or more terminal reactive groups with one of the GLP-2 derivative and a carrier (for example, an immunoglobulin Fc region) such that the complex has the GLP-2 derivative or the carrier attached to one terminal end of the non-peptidyl polymer, and a reactive end group at the other terminal end; and (b) preparing a conjugate by reacting the complex prepared in Step (a) with one of the carrier and the GLP-2 derivative not attached to the complex such that the GLP-2 derivative and the carrier are linked via a non-peptidyl polymer.

The description above applies to the non-peptidyl polymer, the carrier, the GLP-2 derivative, and the linking constitution thereof.

As used herein, the term "complex" refers to an intermediate in which only one of the GLP-2 derivative and the carrier is linked to the non-peptidyl polymer via a covalent bond. A GLP-2 derivative or carrier not attached to the complex may be linked to the terminus of the non-peptidyl polymer of the complex in which the terminus is not linked to the GLP-2 derivative or carrier.

In still another aspect, the present invention provides a long-acting formulation of GLP-2 having increased in vivo durability and stability, which comprises the GLP-2 conjugate.

Meanwhile, the formulation that can increase bioavailability or maintain long-acting activities may include sustained-release formulations using microparticles and nanoparticles using PLGA, hyaluronic acid, chitosan, etc.

Additionally, examples of other forms of formulations that can increase bioavailability or maintain long-acting activities may include implants, inhalations, nasal formulations, and patches.

The GLP-2 conjugate of the present invention can maintain in vivo activities of the conventional GLP-2, and can also increase the blood half-life of the GLP-2 derivative and markedly increase duration of in vivo efficacy of the peptide, and therefore, the GLP-2 conjugate is useful in the treatment of intestinal disease, intestinal injury, and gastrosia.

In still another aspect, the present invention provides a composition, for example, a pharmaceutical composition comprising the GLP-2 derivative and/or the GLP-2 conjugate.

The pharmaceutical composition may be a pharmaceutical composition for preventing or treating one or more diseases selected from intestinal disease, intestinal injury, and gastrosia.

The GLP-2 derivative and the GLP-2 conjugate are as described above.

As used herein, the term "intestinal disease" may refer to short-bowel syndrome, hypersensitive intestinal disease, inflammatory intestinal disease, Crohn's disease, colonitis, colitis, pancreatitis, ileitis, mucositis, or intestine atrophy, but is not limited thereto.

As used herein, the term "gastrosia" may refer to gastrospasm, gastritis, gastric ulcer, duodenitis, or duodenal ulcer, but is not limited thereto.

As used herein, the term "prevention" refers to any activity to suppress or delay the onset of diseases by administering the pharmaceutical composition. The term "treatment" refers to all activities that improve or advantageously change the symptoms of diseases by administering the pharmaceutical composition.

The pharmaceutical composition according to the present invention may include a pharmaceutically acceptable carrier.

As used herein, the term "pharmaceutically acceptable" refers to the properties of having a sufficient amount to exhibit a therapeutic effect and not cause adverse effects, and may be easily determined by those skilled in the art based on factors well known in the medical field, such as the kind of disease, age, weight, health conditions, sex, drug sensitivity of a patient, administration route, administration method, administration frequency, duration of treatment, a drug(s) to be mixed or administered simultaneously, etc.

The pharmaceutically acceptable carrier may include, for oral administration, a binder, a glidant, a disintegrant, an excipient, a solubilizing agent, a dispersant, a stabilizing agent, a suspending agent, a coloring agent, a flavoring agent, etc.; for injections, a buffering agent, a preserving agent, an analgesic, a solubilizing agent, an isotonic agent, a stabilizing agent, etc., which may be combined to be used; and for topical administrations, a base, an excipient, a lubricant, a preserving agent, etc. The formulation type of the pharmaceutical composition of the present invention may be prepared variously by combining with a pharmaceutically acceptable carrier described above. For example, for oral administration, the composition may be formulated into tablets, troches, capsules, elixirs, suspensions, syrups, wafers, etc. For injections, the composition may be formulated into unit-dose ampoules or multi-dose containers. Additionally, the composition may also be formulated into solutions, suspensions, tablets, pills, capsules, sustained-release formulations, etc.

Meanwhile, examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition may further contain a filler, an anti-coagulant, a lubricant, a humectant, a flavoring agent, a preservative, etc.

Additionally, the GLP-2 derivative and/or GLP-2 conjugate of the present invention may be contained in an amount of 0.001 wt % to 10 wt % based on the total weight of the composition of the present invention, but is not particularly limited thereto.

In still another aspect, the present invention provides a method for preventing or treating one or more diseases selected from intestinal disease, intestinal injury, and gastrosia, comprising administering the GLP-2 derivative, the GLP-2 conjugate, and/or the pharmaceutical composition containing the same as an active ingredient to a subject in need thereof.

The GLP-2 derivative, the GLP-2 conjugate, the pharmaceutical composition, the intestinal disease, the intestinal injury, the gastrosia, the prevention, and the treatment are as described above.

As used herein, the term "subject" refers to a subject suspected of having intestinal disease, intestinal injury, or gastrosia, and the subject suspected of having the disease refers to mammals including humans, rats, cattle, etc., which have or are at risk of developing the disease, but any subject which can be treated with the GLP-2 derivative, GLP-2 conjugate, or composition containing the same of the present invention is included without limitation.

As used herein, the term "administration" refers to the introduction of a particular substance into a patient by any appropriate method, and the administration route may be any conventional route that enables delivery of the drug to the target tissue. This may be intraperitoneal administration, intravenous administration, intramuscular administration, subcutaneous administration, intradermal administration, oral administration, local administration, intranasal administration, intrapulmonary administration, intrarectal administration, etc., but is not limited thereto. However, since peptides are digested upon oral administration, active ingredients of a composition for oral administration are preferably coated or formulated for protection against degradation in the stomach, and specifically, may be administered in an injectable form. Additionally, the pharmaceutical composition may be administered using a certain device capable of transporting the active ingredients into a target cell.

Additionally, the pharmaceutical composition of the present invention may be determined based on the types of medicaments used as an active ingredient along with various factors such as the disease to be treated, administration route, age, sex, and weight of a patient, severity of the disease, etc. Since the pharmaceutical composition of the present invention has significantly excellent in vivo duration, the number and frequency of administration of the pharmaceutical composition of the present invention can be significantly reduced.

The total effective dose of the composition of the present invention may be administered to a patient in a single dose or may be administered for a long period of time in multiple doses according to a fractionated treatment protocol. In the pharmaceutical composition of the present invention, the content of the active ingredient may vary depending on the disease severity. Specifically, the total daily dose of the GLP-2 derivative or the GLP-2 conjugate of the present invention may be about 0.0001 mg to 500 mg per 1 kg of body weight of a patient.

However, the effective dose of the GLP-2 derivative or the GLP-2 conjugate is determined considering various factors including patient's age, body weight, health conditions, sex, disease severity, diet, and excretion rate, in addition to administration route and treatment frequency of the pharmaceutical composition. In this regard, those skilled in the art may easily determine the effective dose suitable for the particular use of the pharmaceutical composition of the present invention. The pharmaceutical composition according to the present invention is not particularly limited to the formulation and administration route and mode, as long as it shows the effects of the present invention.

In still another aspect, the present invention provides a use of the GLP-2 derivative or GLP-2 conjugate for the preparation of a medicament.

In one aspect, the medicament may be used for preventing or treating one or more diseases selected from intestinal disease, intestinal injury, and gastrosia, but is not particularly limited thereto.

In still another aspect, the present invention provides a use of the GLP-2 derivative or the GLP-2 conjugate for preventing or treating one or more diseases selected from intestinal disease, intestinal injury, and gastrosia.

The GLP-2 derivative, the GLP-2 conjugate, the intestinal disease, the intestinal injury, and gastrosia are as described above.

The present invention is further illustrated by the following Examples. However, it shall be understood that these Examples are only used to specifically set forth the present invention, and it should not be understood that they are used to limit the present invention in any form.

Example 1: Preparation of CA-GLP-2 KC-PEG (10K)-Immunoglobulin Fc Conjugate or CA-GLP-2 RC-PEG (10K)-Immunoglobulin Fc Conjugate For PEGylation of 10 kDa MAL-ALD PEG (polyethylene glycol having a molecular weight of 10 kDa, wherein the hydrogen at each terminus is modified with a 3-[(3-N-maleimidyl)propanoyl]aminopropyl group and a propylaldehyde group, respectively; NOF Inc., Japan) to the 34$^{th}$ cysteine residue of the CA-GLP-2 KC or CA-GLP-2 RC (CPC, Chinese Peptide Co, China), the reaction was carried out for 1 to 3 hours with the molar ratio of CA-GLP-2 KC or CA-GLP-2 RC to PEG as 1:1 to 2 and the peptide concentration of 1 mg/mL to 3 mg/mL. Herein, the reaction was carried out in a mixed solvent of 50 mM Tris (pH 7.5) and isopropanol. From the reaction solution, the mono-PEGylated CA-GLP-2 KC or mono-PEGylated CA-GLP-2 RC was purified using an SP Sepharose High Performance column (GE, U.S.A.) utilizing a concentration gradient of potassium chloride and a buffer containing ethanol and sodium citrate (pH 2.0).

Thereafter, the reaction was carried out at 2° C. to 8° C. for 12 to 20 hours, with the molar ratio of the purified mono-PEGylated CA-GLP-2 KC or mono-PEGylated CA-GLP-2 RC and the immunoglobulin Fc fragment as 1:2 to 1:6 and the total protein concentration of 30 mg/mL to 35 mg/mL. Herein, the reaction solution contained 20 mM sodium cyanoborohydride ($NaCNBH_3$) which was added as a reducing agent to a 100 mM potassium phosphate buffer (pH 6.0) and isopropanol.

Upon completion of the reaction, the long-acting conjugate of CA-GLP-2 RC (10K PEG) derivative (CA-GLP-2 KC-PEG(10K)-immunoglobulin Fc) and the long-acting conjugate of CA-GLP-2 RC (10K PEG) derivative (CA-GLP-2 RC-PEG(10K)-immunoglobulin Fc), in which the CA-GLP-2 KC or CA-GLP-2 RC is covalently linked to the immunoglobulin Fc by the PEG, were purified from the reaction solution by applying to a Source15Q column (GE, U.S.A.) using the concentration gradient of a bis-Tris buffer (pH 6.5) and sodium chloride, and by applying to a Source 15ISO column (GE, U.S.A.) using the concentration gradient of ammonium sulfate and sodium citrate (pH 5.0 to 5.2). As a result of HPLC reverse analysis, the purity of the conjugates was determined to be 92.9% and 95.6%, respectively, and the result thereof is shown in FIG. 1.

Example 2: Preparation of CA-GLP-2 RK-PEG (3.4K or 10K)-Immunoglobulin Fc Conjugate For PEGylation of 3.4 kDa or 10 kDa ALD(2) PEG (polyethylene glycol having a molecular weight of 3.4 kDa, wherein the hydrogens at each terminus are modified with propylaldehyde groups; NOF Inc., Japan) to the 34$^{th}$ lysine residue of the CA-GLP-2 RK (CPC, Chinese Peptide Co., China), the reaction was carried out at 2° C. to 8° C. for 4 to 16 hours with the molar ratio of CA-GLP-2 RK to PEG as 1:5 to 1:20 and the peptide concentration of 5 mg/mL to 10 mg/mL. Herein, the reaction was carried out in 20 mM HEPES (pH 7.5) and ethanol, and was performed by adding 20 mM sodium cyanoborohydride as a reducing agent. From the reaction solution, the mono-PEGylated CA-GLP-2 RK was purified by using a Source 15S column (GE, U.S.A.) utilizing a concentration gradient of potassium chloride and a buffer containing ethanol and sodium citrate (pH 2.0).

Thereafter, the conjugate of the purified mono-PEGylated CA-GLP-2 RK and immunoglobulin Fc was prepared and purified according to the same reaction and purification conditions as in Example 1. As a result of HPLC reverse phase analysis, the purity of the long-acting conjugate of CA-GLP-2 RK (3.4K PEG) derivative (CA-GLP-2 RK-PEG (3.4K)-immunoglobulin Fc) and the long-acting conjugate of CA GLP-2 RK (10K PEG) derivative (CA-GLP-2 RK-PEG (10K)-immunoglobulin Fc), in which the CA-GLP-2 RK is covalently linked to the immunoglobulin Fc by the PEG, was 94.3% and 92.6%, respectively, and the result thereof is shown in FIG. 1.

Example 3: Preparation of CA-GLP-2 KK-PEG (10K)-Immunoglobulin Fc Conjugate and CA-GLP-2 $K_{AZ}$K-PEG(10K)-Immunoglobulin Fc Conjugate By using CA-GLP-2 KK and CA-GLP-2 $K_{AZ}$K according to the method of Example 2, the long-acting conjugate of CA GLP-2 KK (10K PEG) derivative (CA-GLP-2 KK-PEG (10K)-immunoglobulin Fc) and the long-acting conjugate of CA GLP-2 $K_{AZ}$K (10K PEG) derivative, in which CA-GLP-2 KK or CA-GLP-2 $K_{AZ}$K is covalently linked to the immunoglobulin Fc by PEG, were prepared and purified.

Example 4: Confirmation of In Vitro Activity of GLP-2 Derivative and Long-Acting Conjugate Thereof In order to measure the activities of the GLP-2 derivatives and the long-acting conjugates of GLP-2 derivatives, which had been obtained in the previous Examples, a cell line in which a GLP-2 receptor is transformed was used to measure the cell activity in vitro. The cell line is one that has been transformed to express a human GLP-2 receptor in Chinese hamster ovary (CHO)—K1, and thus is suitable for measuring the activity of GLP-2 (DiscoverX, U.S.A.).

In order to measure the activities of the GLP-2 derivatives and the long-acting conjugates thereof, human GLP-2 and Teduglutide (Gattex®, Shire) were subjected to a 3-fold serial dilution from 166.7 nM to 0.0028 nM; the GLP-2 derivatives were subjected to a 3-fold serial dilution from 500 nM to 0.0085 nM; and the long-acting conjugates of GLP-2 derivatives were subjected to a 3-fold serial dilution from 3000 nM to 0.0508 nM. The culture solution was removed from the cultured CHO-K1 cells, in which the human GLP-2 receptor is expressed, and then each of the serially diluted material was added to the cells in an amount of 5 μL, respectively. Thereafter, the buffer (5 μL) containing a cAMP antibody was added and then the cultivation was conducted at room temperature for 15 minutes. Then, a detection mix (10 μL) containing a cell lysis buffer was added thereto to dissolve the cells and reacted at room temperature for 60 minutes. The cell lysates, upon completion of the reaction, were applied to a LANCE cAMP kit (PerkinElmer, U.S.A.) to calculate the $EC_{50}$ value via accumulated cAMP, and the values were compared with one another. The relative titers compared to human GLP-2 are shown in Table 2.

TABLE 2

| Relative titer ratio of GLP-2 derivative | | | |
|---|---|---|---|
| GLP-2 derivative | In vitro activity compared to human GLP-2 (%) | Conjugate of GLP-2 derivative | In vitro activity compared to human GLP-2 (%) |
| Teduglutide | 147.5 | — | — |
| CA GLP-2 KC | 149.3 | Long-acting conjugate of CA GLP-2 KC (10K PEG) derivative | 9.7 |
| CA GLP-2 KK | 205.6 | Long-acting conjugate of CA GLP-2 KK (10K PEG) derivative | ND |
| CA GLP-2 RC | 120.0 | Long-acting conjugate of CA GLP-2 RC (10K PEG) derivative | 46.0 |
| CA GLP-2 RK | 333.2 | Long-acting conjugate of CA GLP-2 RK (10K PEG) derivative | 52.0 |
| | | Long-acting conjugate of CA GLP-2 RK (3.4K PEG) derivative | 52.6 |

ND = Not determined

It was confirmed that the novel GLP-2 derivatives and long-acting conjugates thereof prepared as described above have a function of activating the GLP-2 receptor, and that the relative potency of the GLP-2 derivatives was remarkably superior compared to that of human GLP-2. Additionally, since it was confirmed that the long-acting conjugate of GLP-2 derivative (CA GLP-2 RK) of SEQ ID NO: 4 and the long-acting conjugate of GLP-2 derivative (CA GLP-2 RC) of SEQ ID NO: 6 had higher activities compared to the long-acting conjugate of GLP-2 derivative (CA GLP-2 KC) of SEQ ID NO: 2, these can be used as materials for treating the desired disease.

Example 5: Confirmation of Pharmacokinetics of Long-Acting Conjugate of GLP-2 Derivative in SD Rat The pharmacokinetics of the long-acting conjugates of GLP-2 derivatives were compared in normal rats.

8-week-old normal rates were divided into a group administering the long-acting conjugate of CA GLP-2 KC (10K PEG) derivative (2.52 mg/kg), a group administering the long-acting conjugate of CA GLP-2 RC (10K PEG) derivative (2.52 mg/kg), a group administering the long-acting conjugate of CA GLP-2 RK (10K PEG) derivative (2.52 mg/kg), and a group administering the long-acting conjugate of CA GLP-2 RK (3.4K PEG) (2.52 mg/kg). The test materials were subcutaneously injected once into the normal rats in each group (3 rats/group). Thereafter, whole blood was obtained by collecting blood samples from the coccygeal vein at 1, 4, 8, 24, 48, 72, 96, 120, 144, and 168 hours for the group administering the long-acting conjugate of CA GLP-2 KC (10K PEG) derivative. In addition, whole blood was obtained by collecting blood samples from the coccygeal vein at 1, 4, 8, 24, 48, 72, 96, 120, 144, 168, 192, 216, 240, 264, 288, 312, and 336 hours for other groups administering the long-acting conjugates of CA GLP-2 derivatives. The whole blood was placed in a 1.5 mL microtube, centrifuged at room temperature at 5,000 rpm for 10 minutes, and then sera were separated and stored at −20° C. Concentrations of the stored sera from each group were quantified using an ELISA analysis method. For the long-acting conjugates of CA GLP-2 derivatives, a biotin-labeled GLP-2 polyclonal antibody (Phoenix Pharmaceuticals, #B-028-14) was bound to a plate coated with Streptadivin (Roche, #11645692001), and then reacted with the serum for 1 hour. After washing, anti-human IgG4-HPR (Alpha Diagonosis, #10124) was added thereto and allowed to react at room temperature for 1 hour. Thereafter, the resultants were subjected to a color reaction using a TMB reagent, and the absorbance was measured at a wavelength of 450 nm. Pharmacokinetic parameters thereof were calculated using the serum concentrations.

As a result, it was confirmed that similar AUC and half-life were exhibited in all the long-acting conjugates of CA GLP-2 derivatives. In particular, for the long-acting conjugate of CA GLP-2 RK (3.4K PEG) derivative, the half-life thereof was actually shortened due to the short PEG, but there was no significant difference in AUC. The result thereof is shown in FIG. 2 and Table 3.

TABLE 3

| Pharmacokinetic parameters of long-acting conjugates of GLP-2 derivatives | | | | | |
|---|---|---|---|---|---|
| GLP-2 derivative | $AUC_{last}$ (ng × hr/mL) | $C_{max}$ (ng/mL) | $T_{max}$ (hr) | $T_{1/2}$ (hr) | $MRT_{last}$ (hr) |
| Long-acting conjugate of CA GLP-2 KC (10K PEG) derivative | 1138923.0 ± 110855.6 | 11745.9 ± 957.4 | 48.0 ± 0.0 | 42.2 ± 3.6 | 74.7 ± 2.0 |

TABLE 3-continued

| Pharmacokinetic parameters of long-acting conjugates of GLP-2 derivatives | | | | | |
|---|---|---|---|---|---|
| GLP-2 derivative | $AUC_{last}$ (ng × hr/mL) | $C_{max}$ (ng/mL) | $T_{max}$ (hr) | $T_{1/2}$ (hr) | $MRT_{last}$ (hr) |
| Long-acting conjugate of CA GLP-2 RC (10K PEG) derivative | 1384949.9 ± 186817.6 | 13350.4 ± 3611.4 | 26.7 ± 20.1 | 54.4 ± 6.9 | 88.9 ± 9.4 |
| Long-acting conjugate of CA GLP-2 RK (10K PEG) derivative | 1329137.5 ± 215962.4 | 12085.8 ± 1970.7 | 32.0 ± 13.9 | 58.6 ± 1.8 | 86.9 ± 3.7 |
| Long-acting conjugate of CA GLP-2 RK (3.4K PEG) derivative | 1058834.3 ± 177030.1 | 12607.7 ± 4030.1 | 13.3 ± 9.2 | 37.0 ± 2.2 | 71.7 ± 11.2 |

$AUC_{last}$: The PK parameter, which represents the drug exposure level in vivo and is closely related to the efficacy/toxicity of drugs (in order for drugs to be effective in vivo, a certain drug exposure level in vivo should be considered; an excessive drug exposure level in vivo may indicate a toxic effect).
$MRT_{last}$: This represents the mean residence time of drugs, which is the average time until drugs disappear in the body. Higher MRT values indicate that drugs are remained in the body for a long period of time, and thus can be evaluated as having a longer duration compared to drugs with lower MRT values.

Example 6. Comparison of Pharmacokinetics Between Long-Acting Conjugate of GLP-2 Derivative and Teduglutide in SD Rat The pharmacokinetics of Teduglutide and the long-acting conjugate of GLP-2 derivative were compared. 8-week-old normal rates were divided into a group administering Teduglutide (2.5 mg/kg) and a group administering the long-acting conjugate of CA GLP-2 RK (3.4K PEG) derivative (0.705 mg/kg). The test materials were subcutaneously injected once into the normal rats in each group (3 rats/group). Thereafter, whole blood was obtained by collecting blood samples from the coccygeal vein at 0.25, 0.5, 1, 1.5, 2, 3, 4, 6, 8, and 24 hours for the group administering Teduglutide; and at 4, 8, 24, 48, 72, 96, 120, 144, 168, 192, 216, 240, 264, 288, 312, and 336 hours for the group administering the long-acting conjugate of CA GLP-2 RK derivative. The whole blood was placed in a 1.5 mL micro-tube, centrifuged at room temperature at 5,000 rpm for 10 minutes, and then sera were separated and stored at −20° C. Concentrations of the stored sera from each group were quantified using an ELISA analysis method. For Teduglutide, a GLP-2 ELISA Kit (Alpco, #48-GP2HU-E01.1) was used. For the long-acting conjugate of CA GLP-2 RK derivative, a biotin-labeled GLP-2 polyclonal antibody (Phoenix Pharmaceuticals, #B-028-14) was bound to a plate coated with Streptavidin (Roche, #11645692001), and then reacted with the serum for 1 hour. After washing, anti-human IgG4-HPR (Alpha Diagnosis, #10124) was added thereto and allowed to react at room temperature for 1 hour. Thereafter, the resultants were subjected to a color reaction using a TMB reagent, and the absorbance was measured at a wavelength of 450 nm. Pharmacokinetic parameters thereof were calculated using the serum concentrations.

As a result, it was confirmed that both AUC and half-life of the long-acting conjugate of CA GLP-2 RK derivative were significantly increased compared to those of Teduglutide. The result thereof is shown in FIG. 3 and Table 4.

TABLE 4

| Pharmacokinetic parameters of Teduglutide and long-acting conjugate of GLP-2 derivative | | | | | |
|---|---|---|---|---|---|
| GLP-2 derivative | $AUC_{last}$ (ng × hr/mL) | $C_{max}$ (ng/mL) | $T_{max}$ (hr) | $T_{1/2}$ (hr) | $MRT_{last}$ (hr) |
| Teduglutide | 2596.6 ± 580.7 | 1675.5 ± 744.0 | 0.7 ± 0.3 | 0.6 ± 0.1 | 1.4 ± 0.1 |
| Long-acting conjugate of CA GLP-2 RK derivative | 199738.9 ± 28544.5 | 2442.1 ± 392.6 | 24.0 ± 0.0 | 42.3 ± 3.4 | 71.1 ± 3.1 |

Example 7: Confirmation of Effect of Increasing In Vivo Intestinal Weight of Long-Acting Conjugate of GLP-2 Derivative in Normal Mice The effects of increasing in vivo intestinal weight of Teduglutide and the long-acting conjugate of GLP-2 derivative were examined in normal mice.

7-week-old C57BL/6 mice were divided into each of a group administering a vehicle, a group administering Teduglutide (7.5 & 15 nmol/kg/BID), and a group administering the long-acting conjugate of CA GLP-2 RK(3.4K PEG) derivative (4.15, 7.5, 15, 30 nmol/kg/Q2D). Five mice were placed in each group and autopsied after 13 days of the administrations. The small intestines were perfused, and the weight of the small intestines and the length of the villi within the small intestines were measured.

As a result, in both Teduglutide and the long-acting conjugate of CA GLP-2 RK derivative, the weight of the small intestines was increased in a dose-dependent manner (FIG. 4(A)), and it could be derived that the increase of the weight of the small intestines is due to the increase in the length of the villi based on the fact that the increase of the intestinal weight is associated with the increase in the villi length (FIG. 4(B)). The high-dose administration group (15 nmol/kg/BID), which is known to exhibit the maximum efficacy of Teduglutide, was similar to the low-dose administration group (4.15 nmol/kg/Q2D) of the group administering the long-acting conjugate of the CA GLP-2 RK derivative, and it was confirmed that the long-acting conjugate of the CA GLP-2 RK derivative had an effect exceeding the maximum efficacy of Teduglutide in a dose-dependent manner. The result thereof is shown in FIG. 4(A) and FIG. 4(B).

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A glucagon-like peptide-2 (GLP-2) conjugate, wherein a GLP-2 derivative and an immunoglobulin Fc region are each covalently linked via a non-peptidyl polymer at both termini of the non-peptidyl polymer, wherein the GLP-2 derivative consists of the amino acid sequence of SEQ ID NO: 4;

wherein the non-peptidyl polymer is polyethylene glycol, wherein a molecular weight of the non-peptidyl polymer is in a range of 3.4 kDa to 10 kDa; and wherein one end of the non-peptidyl polymer is conjugated to the immunoglobulin Fc region and the other end of the non-peptidyl polymer is conjugated to lysine of the GLP-2 derivative at position 34 of SEQ ID NO: 4.

2. The GLP-2 conjugate according to claim 1, wherein the immunoglobulin Fc region is non-glycosylated.

3. The GLP-2 conjugate according to claim 1, wherein the immunoglobulin Fc region comprises a hinge region.

4. The GLP-2 conjugate according to claim 1, wherein the immunoglobulin Fc region is an IgG4 Fc region.

5. The GLP-2 conjugate according to claim 1, wherein the molecular weight of the non-peptidyl polymer is 3.4 kDa or 10 kDa.

6. A method for preparing the GLP-2 conjugate of claim 1, comprising:

(a) preparing a complex by reacting a non-peptidyl polymer having two or more terminal reactive groups with one of the GLP-2 derivative as defined in claim 1 and an immunoglobulin Fc region such that the complex has the GLP-2 derivative or the immunoglobulin Fc region attached to one terminal end of the non-peptidyl polymer, and a reactive group at the other terminal end; and (b) preparing a conjugate by reacting the complex prepared in step (a) with one of the immunoglobulin Fc region and the GLP-2 derivative not attached to the complex such that the GLP-2 derivative and the immunoglobulin Fc region are linked via the non-peptidyl polymer, wherein the non-peptidyl polymer is polyethylene glycol, wherein a molecular weight of the non-peptidyl polymer is in a range of 3.4 kDa to 10 kDa, and wherein one end of the non-peptidyl polymer is conjugated to the immunoglobulin Fc region and the other end of the non-peptidyl polymer is conjugated to lysine of the GLP-2 derivative at position 34 of SEQ ID NO: 4.

7. The method according to claim 6, wherein the non-peptidyl polymer comprises one or more reactive groups selected from the group consisting of an aldehyde group, a propionaldehyde group, a butyraldehyde group, a maleimide group, and a succinimide derivative.

8. The method according to claim 7, wherein the succinimide derivative is succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

9. A method for treating one or more diseases selected from intestinal disease, intestinal injury, and gastrosia, comprising administering an effective amount of a composition comprising the GLP-2 conjugate according to claim 1 to a subject in need thereof.

10. The method according to claim 9, wherein the intestinal disease is short-bowel syndrome, hypersensitive intestinal disease, inflammatory intestinal disease, Crohn's disease, colonitis, colitis, pancreatitis, ileitis, mucositis, or intestine atrophy.

11. The method according to claim 9, wherein the gastrosia is stomach cramps, gastritis, gastric ulcer, duodenitis, or duodenal ulcer.

* * * * *

SEQUENCE LISTING

```
<160> NUMBER OF SEQ ID NOS: 9

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp


<210> SEQ ID NO 2
<211> LENGTH: 34
<212> TYPE: PRT
<213> ORGANISM: Artificial Sequence
<220> FEATURE:
<223> OTHER INFORMATION: GLP-2 derivative
<220> FEATURE:
<221> NAME/KEY: MISC_FEATURE
<222> LOCATION: (1)
<223> OTHER INFORMATION: Xaa is imidazoacetyldeshistidine

<400> SEQUENCE: 2

Xaa Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Cys


<210> SEQ ID NO 3
<211> LENGTH: 34
<212> TYPE: PRT
<213> ORGANISM: Artificial Sequence
<220> FEATURE:
<223> OTHER INFORMATION: GLP-2 derivative
<220> FEATURE:
<221> NAME/KEY: MISC_FEATURE
<222> LOCATION: (1)
<223> OTHER INFORMATION: Xaa is imidazoacetyldeshistidine

<400> SEQUENCE: 3

Xaa Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Lys


<210> SEQ ID NO 4
<211> LENGTH: 34
<212> TYPE: PRT
<213> ORGANISM: Artificial Sequence
<220> FEATURE:
```

```
<223> OTHER INFORMATION: GLP-2 derivative
<220> FEATURE:
<221> NAME/KEY: MISC_FEATURE
<222> LOCATION: (1)
<223> OTHER INFORMATION: Xaa is imidazoacetyldeshistidine

<400> SEQUENCE: 4

Xaa Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Arg Ile Thr
            20                  25                  30

Asp Lys


<210> SEQ ID NO 5
<211> LENGTH: 34
<212> TYPE: PRT
<213> ORGANISM: Artificial Sequence
<220> FEATURE:
<223> OTHER INFORMATION: GLP-2 derivative
<220> FEATURE:
<221> NAME/KEY: MISC_FEATURE
<222> LOCATION: (1)
<223> OTHER INFORMATION: Xaa is imidazoacetyldeshistidine
<220> FEATURE:
<221> NAME/KEY: MISC_FEATURE
<222> LOCATION: (34)
<223> OTHER INFORMATION: Xaa is 6-azidolysine

<400> SEQUENCE: 5

Xaa Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Xaa


<210> SEQ ID NO 6
<211> LENGTH: 34
<212> TYPE: PRT
<213> ORGANISM: Artificial Sequence
<220> FEATURE:
<223> OTHER INFORMATION: GLP-2 derivative
<220> FEATURE:
<221> NAME/KEY: MISC_FEATURE
<222> LOCATION: (1)
<223> OTHER INFORMATION: Xaa is imidazoacetyldeshistidine

<400> SEQUENCE: 6

Xaa Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Arg Ile Thr
            20                  25                  30

Asp Cys


<210> SEQ ID NO 7
<211> LENGTH: 34
<212> TYPE: PRT
<213> ORGANISM: Artificial Sequence
<220> FEATURE:
<223> OTHER INFORMATION: GLP-2 derivative
<220> FEATURE:
<221> NAME/KEY: MISC_FEATURE
<222> LOCATION: (1)
<223> OTHER INFORMATION: Xaa is imidazoacetyldeshistidine
<220> FEATURE:
<221> NAME/KEY: MISC_FEATURE
<222> LOCATION: (2)
<223> OTHER INFORMATION: Xaa is Aib(2-aminoisobutyric acid)
```

```
<400> SEQUENCE: 7

Xaa Xaa Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Cys


<210> SEQ ID NO 8
<211> LENGTH: 34
<212> TYPE: PRT
<213> ORGANISM: Artificial Sequence
<220> FEATURE:
<223> OTHER INFORMATION: GLP-2 derivative
<220> FEATURE:
<221> NAME/KEY: MISC_FEATURE
<222> LOCATION: (2)
<223> OTHER INFORMATION: Xaa is Aib(2-aminoisobutyric acid)

<400> SEQUENCE: 8

His Xaa Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Cys


<210> SEQ ID NO 9
<211> LENGTH: 34
<212> TYPE: PRT
<213> ORGANISM: Artificial Sequence
<220> FEATURE:
<223> OTHER INFORMATION: GLP-2 derivative
<220> FEATURE:
<221> NAME/KEY: MISC_FEATURE
<222> LOCATION: (1)
<223> OTHER INFORMATION: Xaa = Histidine, imidazoacetyldeshistidine,
      desaminohistidine, beta-hydroxyimidazopropionyldeshistidine,
      N-dimethylhistidine, or beta-carboxyimidazopropionyldeshistidine
<220> FEATURE:
<221> NAME/KEY: MISC_FEATURE
<222> LOCATION: (2)
<223> OTHER INFORMATION: Xaa is Alanine, Glycine, or
      Aib(2-aminoisobutyric acid)
<220> FEATURE:
<221> NAME/KEY: MISC_FEATURE
<222> LOCATION: (30)
<223> OTHER INFORMATION: Xaa is Lysine, or Arginine
<220> FEATURE:
<221> NAME/KEY: MISC_FEATURE
<222> LOCATION: (34)
<223> OTHER INFORMATION: Xaa is absent, Lysine, Arginine, Glutamine,
      Histidine, 6-azidolysine, or Cysteine

<400> SEQUENCE: 9

Xaa Xaa Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Xaa Ile Thr
            20                  25                  30

Asp Xaa
```